US012605169B1

(12) United States Patent
Evans et al.

(10) Patent No.: US 12,605,169 B1
(45) Date of Patent: Apr. 21, 2026

(54) OSTEOCHONDRAL TRANSFER SYSTEMS AND METHODS

(71) Applicant: University of Utah Research Foundation, Salt Lake City, UT (US)

(72) Inventors: Zackery Evans, Woods Cross, UT (US); T. Wade Fallin, Hyde Park, UT (US); Travis G. Maak, Park City, UT (US); Charles L. Saltzman, Salt Lake City, UT (US); Austin Hickey, South Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 19/301,948

(22) Filed: Aug. 16, 2025

Related U.S. Application Data

(60) Provisional application No. 63/819,378, filed on Jun. 6, 2025.

(51) Int. Cl.
*A61B 17/17* (2006.01)
*A61B 17/15* (2006.01)
*A61F 2/46* (2006.01)

(52) U.S. Cl.
CPC .............. *A61B 17/17* (2013.01); *A61B 17/15* (2013.01); *A61F 2/4601* (2013.01)

(58) Field of Classification Search
CPC . A61B 17/16; A61B 17/1626; A61B 17/1637; A61B 17/1633; A61B 17/1697; A61B 17/1675; A61B 17/1664; A61B 17/1635; A61B 90/03
See application file for complete search history.

(56) References Cited

U.S. PATENT DOCUMENTS

| | | | |
|---|---|---|---|
| 1,493,240 | A | 5/1924 | Bohn |
| 2,485,531 | A | 10/1949 | Dzus et al. |
| 2,919,692 | A | 1/1960 | Wolfgang |
| 4,069,824 | A | 1/1978 | Weinstock |
| 4,632,101 | A | 12/1986 | Freedland |
| 4,649,918 | A | 3/1987 | Pegg |
| 4,696,308 | A | 9/1987 | Meller et al. |

(Continued)

FOREIGN PATENT DOCUMENTS

WO      WO2011026164 A1      3/2011

OTHER PUBLICATIONS

Anthrex, IntraOsseous BioPlasty® (IOBP®) Surgical Technique for a Bone Marrow Lesion of the Hip, https://www.arthrex.com/resources/animation/PvHgV7tD0Ui-OgF7h3Polw/intraosseous-bioplasty-iobp-surgical-technique-for-a-bone-marrow-lesion-of-the-hip, accessed on or before Mar. 28, 2022.

(Continued)

*Primary Examiner* — Christopher J Beccia
(74) *Attorney, Agent, or Firm* — David Meibos; Maywood IP Law

(57) ABSTRACT

A system may be provided for osteochondral defect repair, and may include a guide with a first leg, a second leg, a third leg, a fourth leg, and a guide feature. The first leg, the second leg, the third leg, and the fourth leg may each have a distal tip. The distal tips of the first leg, the second leg, the third leg, and the fourth leg may lie in a plane. The guide feature may be oriented to define a working axis, perpendicular to the plane, along which a cutter is movable to remove bone and cartilage from a first bone.

34 Claims, 17 Drawing Sheets

(56) References Cited

U.S. PATENT DOCUMENTS

| | | |
|---|---|---|
| 4,782,833 A | 11/1988 | Einhorn |
| 4,913,143 A | 4/1990 | Oloff |
| 5,098,433 A | 3/1992 | Freedland |
| 5,197,967 A | 3/1993 | Wilson |
| 5,324,300 A | 6/1994 | Elias |
| 5,330,480 A | 7/1994 | Meloul |
| 5,346,497 A | 9/1994 | Simon |
| 5,423,823 A | 6/1995 | Schmieding |
| 5,478,353 A | 12/1995 | Yoon |
| 5,556,399 A | 9/1996 | Huebner |
| 5,674,247 A | 10/1997 | Sohn |
| 5,782,835 A | 7/1998 | Hart |
| 5,885,293 A | 3/1999 | McDevitt |
| 5,893,850 A | 4/1999 | Cachia |
| 5,919,196 A | 7/1999 | Bobic |
| 5,921,987 A * | 7/1999 | Stone ............... A61F 2/30756 606/80 |
| 5,928,238 A | 7/1999 | Scarborough |
| 6,017,348 A | 1/2000 | Hart |
| 6,027,504 A | 2/2000 | McGuire |
| 6,068,648 A | 5/2000 | Cole |
| 6,102,934 A | 8/2000 | Li |
| 6,110,209 A | 8/2000 | Stone |
| 6,146,385 A | 11/2000 | Torrie et al. |
| 6,193,722 B1 | 2/2001 | Zech |
| 6,200,319 B1 | 3/2001 | Storer |
| 6,358,253 B1 | 3/2002 | Torrie |
| 6,395,011 B1 | 5/2002 | Johanson |
| 6,591,581 B2 | 7/2003 | Schmieding |
| 6,592,588 B1 | 7/2003 | Bobic |
| 6,607,561 B2 | 8/2003 | Brannon |
| 6,682,535 B2 | 1/2004 | Hoogland |
| 6,767,354 B2 | 7/2004 | Johanson |
| 6,857,520 B2 | 2/2005 | Salazar |
| 6,884,245 B2 | 4/2005 | Spranza, III |
| 6,942,669 B2 | 9/2005 | Kurc |
| 7,097,654 B1 | 8/2006 | Freedland |
| 7,445,595 B2 | 11/2008 | Brannon |
| 7,513,901 B2 | 4/2009 | Scifert |
| 7,537,597 B2 | 5/2009 | Salazar |
| RE40,796 E | 6/2009 | O'Neill |
| 7,591,820 B2 | 9/2009 | Schmieding et al. |
| 7,819,888 B2 | 10/2010 | Johanson |
| 7,824,711 B2 | 11/2010 | Kizer |
| 7,879,040 B2 | 2/2011 | Bharadwaj |
| 7,896,880 B2 | 3/2011 | Bonutti |
| 8,043,315 B2 | 10/2011 | Shepard |
| 8,118,872 B2 | 2/2012 | Trudeau |
| 8,162,967 B1 | 4/2012 | Kaiser |
| 8,221,423 B2 | 7/2012 | Gil |
| 8,251,998 B2 | 8/2012 | Hoeppner |
| 8,382,762 B2 | 2/2013 | Brannon |
| 8,403,959 B2 | 3/2013 | Döllinger |
| 8,414,585 B2 | 4/2013 | Meneghini |
| 8,454,652 B1 | 6/2013 | Cohen |
| 8,470,013 B2 | 6/2013 | Duggal |
| 8,497,121 B2 | 7/2013 | Yao |
| 8,518,433 B2 | 8/2013 | Kizer |
| 8,585,744 B2 | 11/2013 | Duggal et al. |
| 8,777,956 B2 | 7/2014 | Hoeppner |
| 8,801,716 B2 | 8/2014 | Meridew |
| 8,814,882 B2 | 8/2014 | Oostman, Jr. et al. |
| 8,828,067 B2 | 9/2014 | Tipirneni |
| 8,845,644 B1 | 9/2014 | Verhoogen |
| 8,926,615 B2 | 1/2015 | Ek |
| 8,992,568 B2 | 3/2015 | Duggal |
| 8,998,918 B2 | 4/2015 | Jamali |
| 9,011,503 B2 | 4/2015 | Duggal et al. |
| 9,084,465 B2 | 7/2015 | Oostman, Jr. |
| 9,119,646 B2 | 9/2015 | Sharkey |
| 9,173,694 B2 | 11/2015 | Kleiner |
| 9,186,380 B2 | 11/2015 | Shi |
| 9,387,019 B2 | 7/2016 | Duggal |
| 9,393,062 B2 | 7/2016 | O'Halloran |
| 9,532,876 B2 | 1/2017 | Sharkey |
| 9,572,686 B2 | 2/2017 | Meridew |
| 9,707,081 B2 | 7/2017 | Sharkey |
| 9,757,135 B1 | 9/2017 | Kelley |
| 9,782,196 B2 | 10/2017 | Bradica |
| 9,855,393 B2 | 1/2018 | Schmieding |
| 9,901,355 B2 | 2/2018 | Bourque |
| 9,913,721 B2 | 3/2018 | Sharkey |
| 9,925,068 B2 | 3/2018 | Bays et al. |
| 9,937,057 B2 | 4/2018 | Gage |
| 9,962,201 B2 | 5/2018 | Duggal |
| 10,058,369 B2 | 8/2018 | O'Halloran et al. |
| 10,130,343 B2 | 11/2018 | Miller |
| 10,159,470 B2 | 12/2018 | Weeney |
| 10,231,846 B2 | 3/2019 | Popejoy |
| 10,300,170 B2 | 5/2019 | Masinaei |
| 10,524,775 B2 | 1/2020 | Benedict |
| 10,548,693 B2 | 2/2020 | Wang |
| 10,687,880 B2 | 6/2020 | DeRidder |
| 10,729,549 B2 | 8/2020 | Schmieding |
| 10,857,001 B2 | 12/2020 | Popejoy |
| 10,912,573 B2 | 2/2021 | Sweitzer |
| 10,945,776 B2 | 3/2021 | Elser |
| 10,973,532 B2 | 4/2021 | Miller |
| 11,020,244 B2 | 6/2021 | Bays et al. |
| 11,039,871 B2 | 6/2021 | Lee |
| 11,090,032 B2 | 8/2021 | Miller |
| 11,116,646 B2 | 9/2021 | Greenhalgh et al. |
| 11,185,339 B2 | 11/2021 | Perez |
| 2002/0010471 A1 | 1/2002 | Wironen |
| 2002/0099382 A1 | 7/2002 | Salazar |
| 2003/0055431 A1 | 3/2003 | Brannon |
| 2004/0002764 A1 | 1/2004 | Gainor |
| 2004/0030343 A1 | 2/2004 | Kurc |
| 2004/0034359 A1 | 2/2004 | Schmieding |
| 2004/0034437 A1 | 2/2004 | Schmieding |
| 2004/0210246 A1 | 10/2004 | Johanson |
| 2005/0131313 A1 | 6/2005 | Mikulka et al. |
| 2005/0178251 A1 | 8/2005 | Holland-Letz |
| 2005/0196460 A1 | 9/2005 | Malinin |
| 2005/0240188 A1 | 10/2005 | Chow |
| 2006/0173476 A1 | 8/2006 | Bradica et al. |
| 2006/0195122 A1 | 8/2006 | Vibe-Hansen |
| 2006/0264954 A1 | 11/2006 | Sweeney |
| 2007/0043376 A1 | 2/2007 | Leatherbury et al. |
| 2007/0123892 A1 | 5/2007 | Ries |
| 2007/0270711 A1 * | 11/2007 | Gil ..................... A61B 17/1635 600/567 |
| 2008/0167652 A1 | 7/2008 | Reinhard |
| 2008/0262616 A1 | 10/2008 | McKay |
| 2008/0269895 A1 | 10/2008 | Steinwachs et al. |
| 2009/0054906 A1 | 2/2009 | Walthall et al. |
| 2009/0149707 A1 | 6/2009 | Brannon |
| 2009/0209964 A1 | 8/2009 | Yeung |
| 2009/0274996 A1 | 11/2009 | Miller |
| 2009/0306671 A1 | 12/2009 | McCormack |
| 2010/0094361 A1 | 4/2010 | Meneghini |
| 2011/0137356 A1 | 6/2011 | Kollmer |
| 2011/0177472 A1 | 7/2011 | Lee |
| 2011/0184234 A1 | 7/2011 | Lopez et al. |
| 2011/0213422 A1 | 9/2011 | Gannoe |
| 2011/0218387 A1 | 9/2011 | Lamson |
| 2011/0306983 A1 | 12/2011 | O'Halloran |
| 2012/0016192 A1 | 1/2012 | Jansen et al. |
| 2012/0045731 A1 | 2/2012 | Singh |
| 2012/0053641 A1 | 3/2012 | Meridew |
| 2012/0116532 A1 | 5/2012 | Forsell |
| 2012/0198972 A1 | 8/2012 | Nino |
| 2012/0237558 A1 | 9/2012 | Kizer |
| 2013/0098942 A1 | 4/2013 | Greter |
| 2013/0144292 A1 | 6/2013 | To |
| 2013/0144295 A1 | 6/2013 | To |
| 2013/0144320 A1 | 6/2013 | To |
| 2014/0074103 A1 | 3/2014 | Mandeen |
| 2014/0088712 A1 | 3/2014 | Gage |
| 2014/0228641 A1 | 8/2014 | Gettman |
| 2014/0257420 A1 | 9/2014 | Fox |
| 2014/0309641 A1 | 10/2014 | Bourque |
| 2014/0350585 A1 | 11/2014 | Meridew |
| 2014/0358170 A1 | 12/2014 | To et al. |

(56)                References Cited

U.S. PATENT DOCUMENTS

| | | |
|---|---|---|
| 2014/0358186 A1 | 12/2014 | Frock |
| 2015/0105696 A1* | 4/2015 | Litke .................. A61F 2/30756 |
| | | 600/587 |
| 2016/0066946 A1 | 3/2016 | To et al. |
| 2017/0143351 A1 | 5/2017 | DeVitre |
| 2017/0238983 A1 | 8/2017 | Kukla |
| 2018/0104062 A1 | 4/2018 | Chen |
| 2018/0110531 A1 | 4/2018 | Arthurs |
| 2018/0147071 A1 | 5/2018 | Budyansky |
| 2019/0117403 A1 | 4/2019 | Schmieding |
| 2019/0290439 A1 | 9/2019 | Marionneaux |
| 2019/0298482 A1 | 10/2019 | Hensler |
| 2019/0328548 A1 | 10/2019 | Bake |
| 2019/0388100 A1 | 12/2019 | Perez |
| 2020/0100800 A1 | 4/2020 | Seykora |
| 2020/0121463 A1 | 4/2020 | Yoshikawa |
| 2020/0188556 A1 | 6/2020 | Kelly |
| 2020/0275963 A1 | 9/2020 | Schlachter |
| 2020/0275965 A1 | 9/2020 | DeRidder |
| 2020/0330080 A1 | 10/2020 | Brewer |
| 2020/0360068 A1 | 11/2020 | Dewey |
| 2021/0052397 A1 | 2/2021 | Popejoy et al. |
| 2021/0259710 A1 | 8/2021 | Mirochinik et al. |
| 2021/0282940 A1 | 9/2021 | Bays |
| 2023/0301646 A1 | 9/2023 | Duggal |

OTHER PUBLICATIONS

Anthrex, Illiac Crest Bone Graft Harvesting Surgical Technique, https://www.arthrex.com/resources/surgical-technique-guide/IMt9Lft52k-pnwFD9v67TA/iliac-crest-bone-graft-harvesting, accessed on or before Mar. 28, 2022.

Anthrex, Autograft OATS 2.0 Set Surgical Technique, https://www.arthrex.com/resources/surgical-technique-guide/sijkOfkEEeCRTQBQVoRHOw/autograft-oats-20-set, accessed on or before Mar. 28, 2022.

Fanelli, ACL Revision Using Revision Dowels and Demineralized Cortical Fibers, CONMED, Nov. 18, 2013, https://www.youtube.com/watch?v=-156M492rVQ.

Becton Dickinson, Jamshidi Bone Marrow Biopsy Needles Overview, https://www.bd.com/en-us/resource-and-education/documentation-landing-page?heroSearchValue=Jamshidi%20overview&lastUpdate=all-dates, accessed on or before Mar. 28, 2022.

Knight, Vexim Rebalancing Spine, Animation of the Spine Jack Technique for the reconstruction of osteoporotic vertebral fractures, May 11, 2014, https://www.youtube.com/watch?v=v0iUcGIRD_0.

Arthrex, Large Allograft System, "Allograft OATS Surgical Technique Animation", found at https://www.youtube.com/watch?v=Boqi610NOLY.

Arthrex, Allograft OATS Technique of the Trochlea, Revision Date May 2017, https://www.arthrex.com/resources/VID1-00850-EN/allograft-oatstechnique-of-thetrochlea?referringteam=orthobiologics.

Johnson & Johnson and DePuy Synthes, "COR Precision Targeting Cartilage Repair System: Arthroscopic Technique for Repair of Osteochondral Defects", https://www.jnjmedtech.com/en-US/product/cor-precision-targeting-system.

Arthrex, "Autograft OATS® 2.0 Set" 2020 (8 pages).

Arthrex, "Allograft OATS® System for Articular Cartilage Restoration: Surgical Technique", 2020 (8 pages).

MTF Sports Medicine, "ACT™ Allograft Cartilage Transplant Surgical Technique" (2 pages).

JRF Ortho, "Articular Cartilage Resurfacing Single Osteochondral Allograft Core Surgical Technique", 2024, Centennial, CO (8 pages).

RTI Surgical—"PACK (Precision Allograft Cartilage Kit) Articular Cartilage Resurfacing, Osteochondral Allograft Plug Surgical Technique", 2019 (12 pages).

* cited by examiner

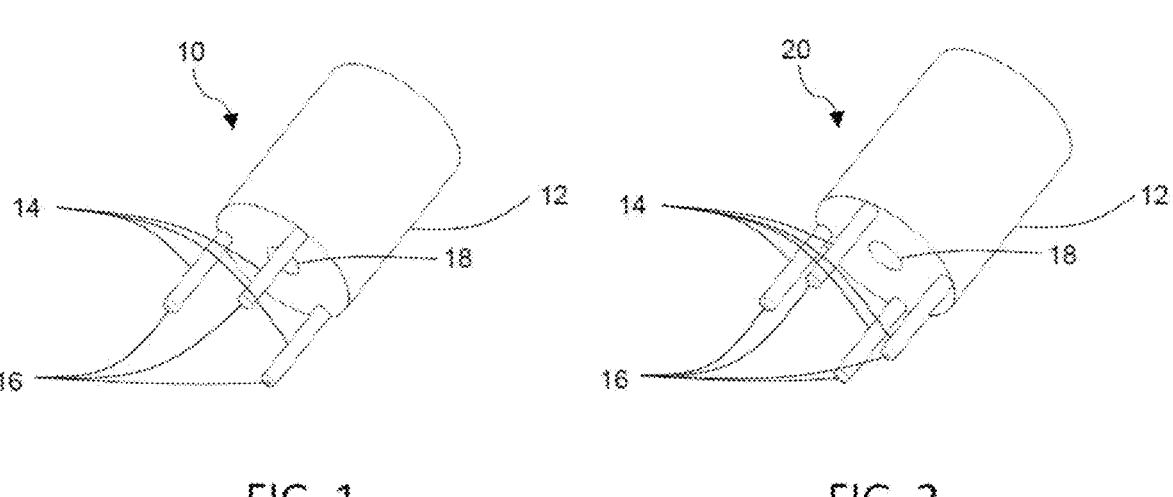
FIG. 1                                    FIG. 2
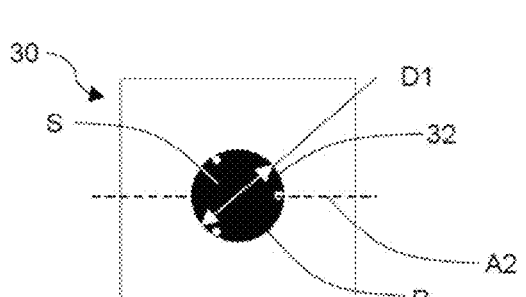
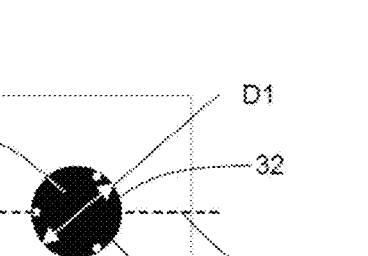
FIG. 3A                                   FIG. 3C
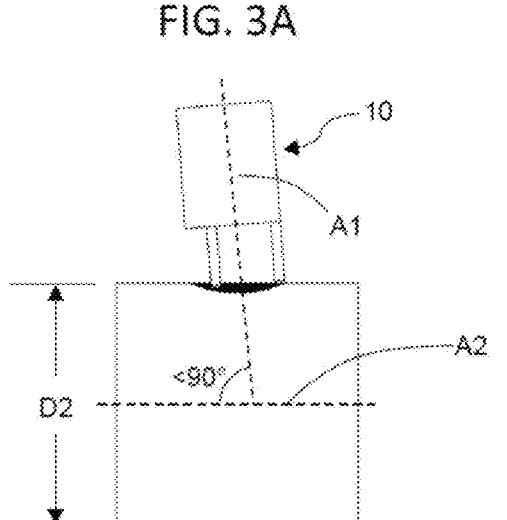
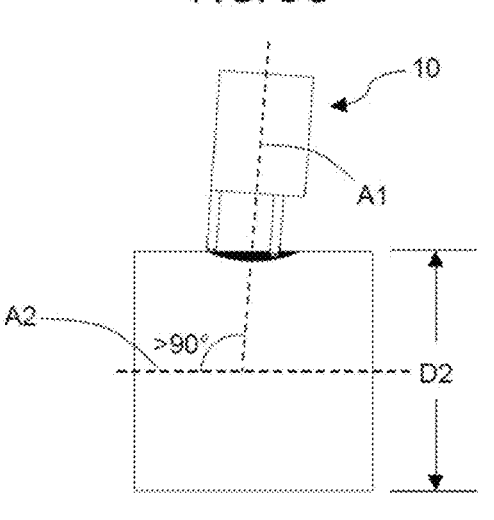
FIG. 3B                                   FIG. 3D

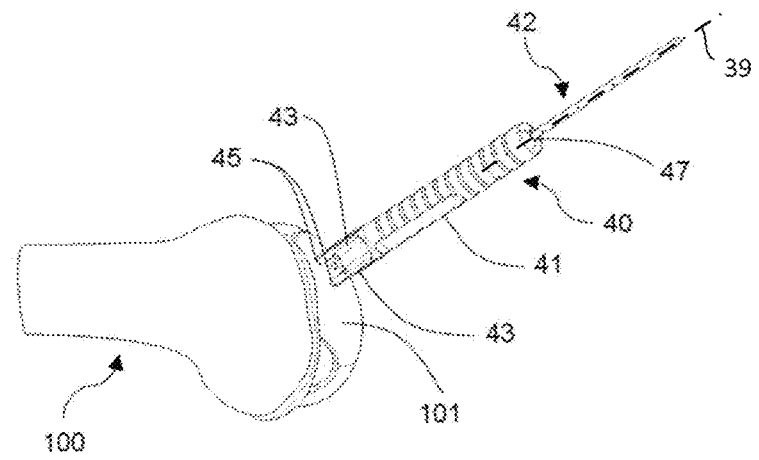
FIG. 6
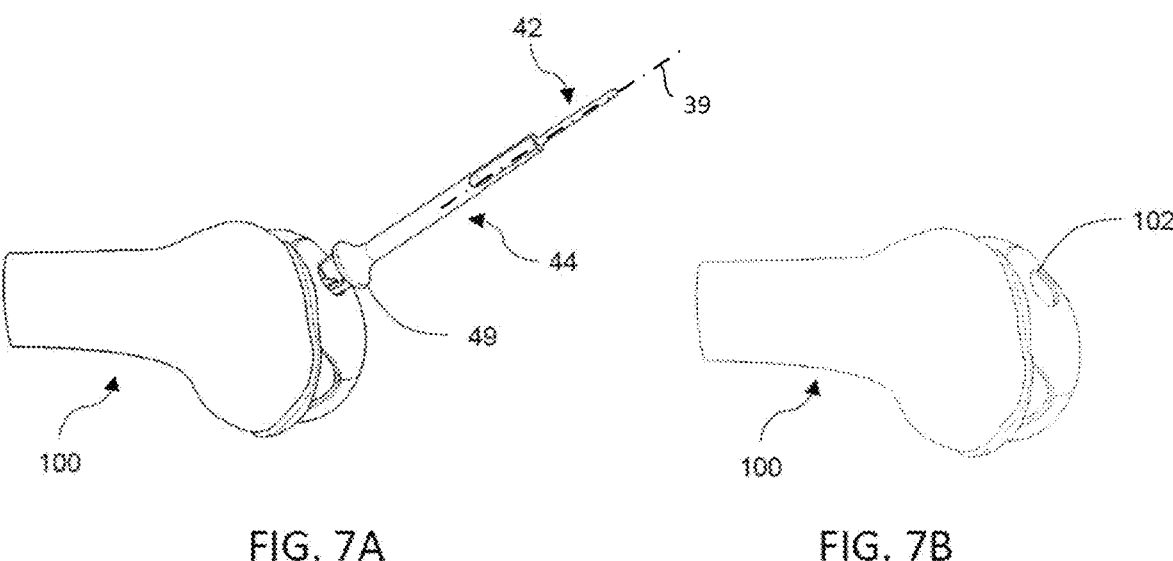
FIG. 7A                    FIG. 7B

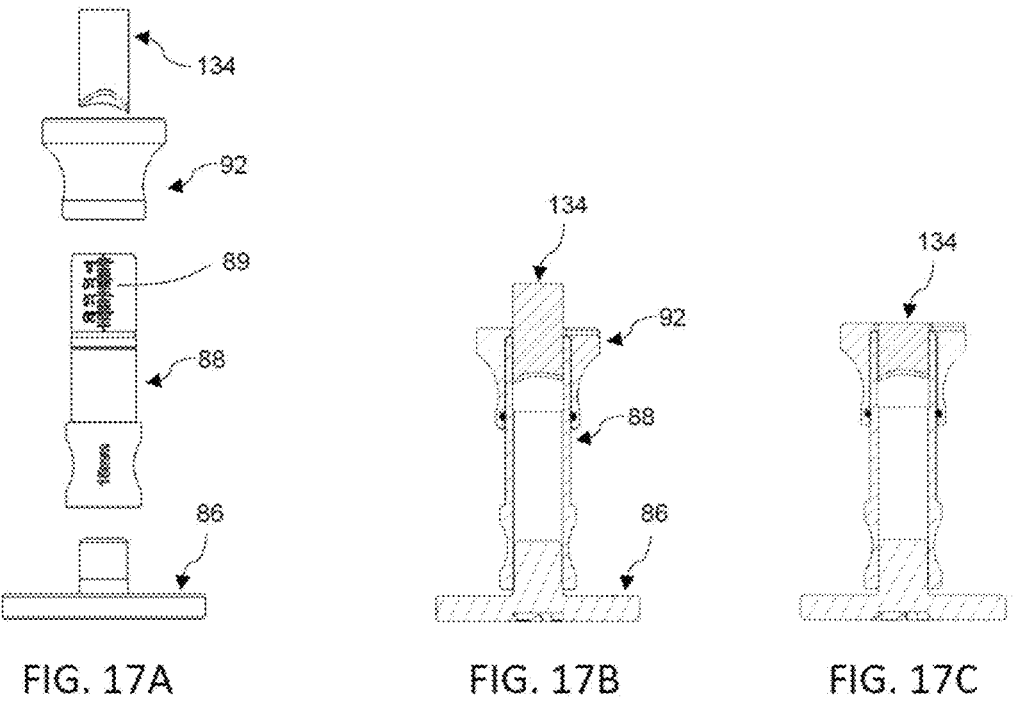
FIG. 17A                FIG. 17B                FIG. 17C
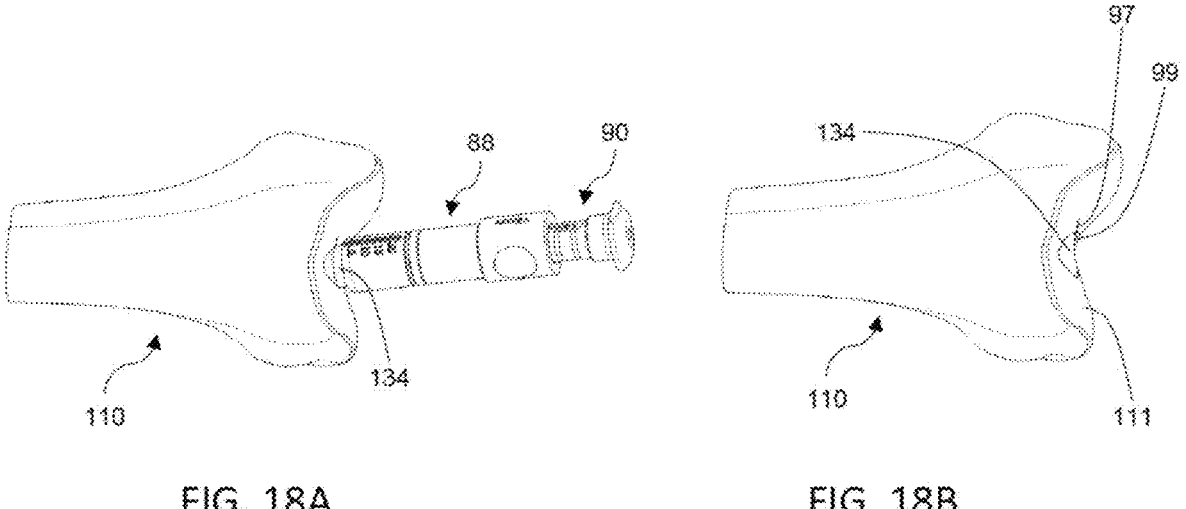
FIG. 18A                                FIG. 18B

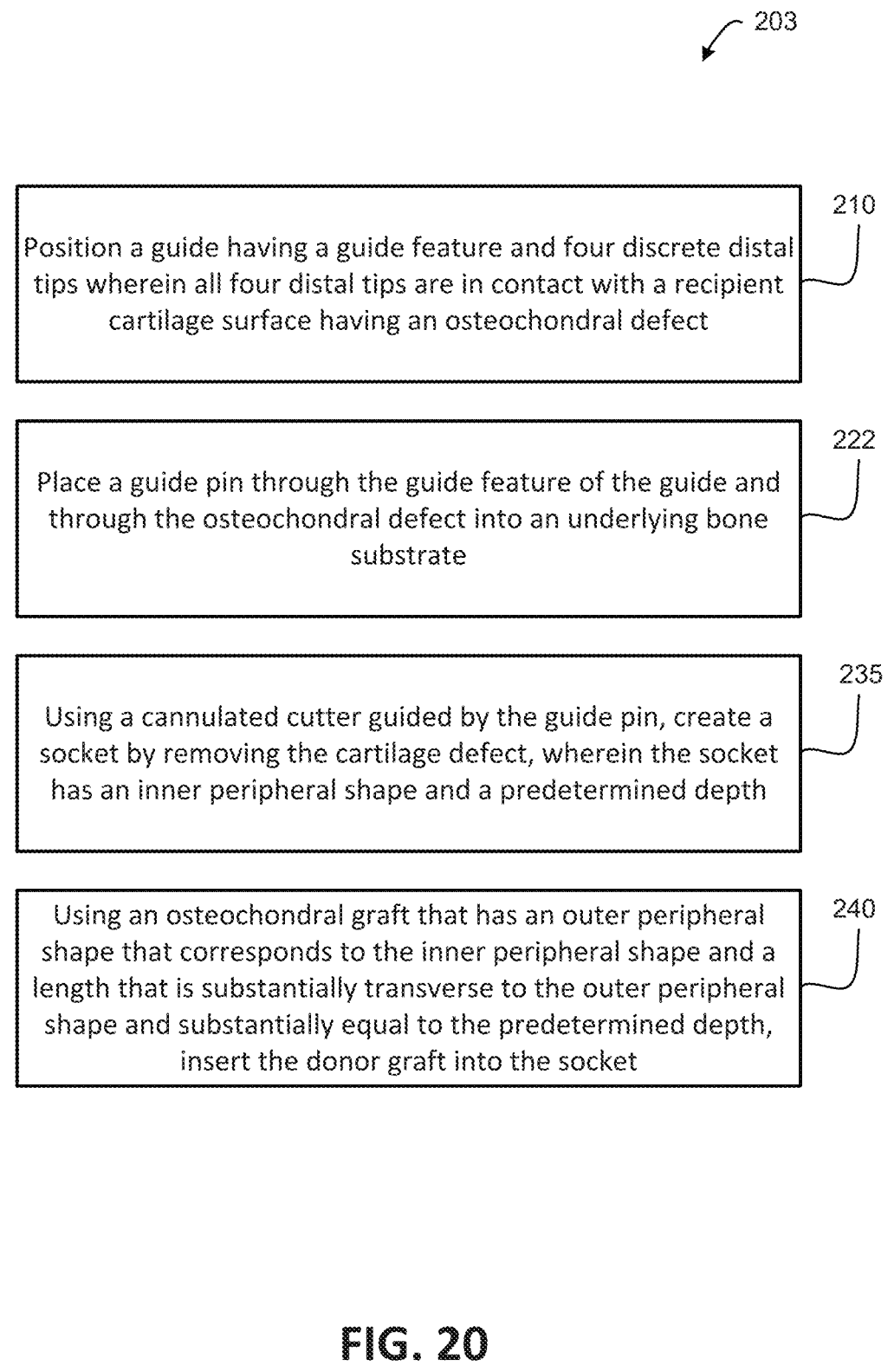

203

210
Position a guide having a guide feature and four discrete distal tips wherein all four distal tips are in contact with a recipient cartilage surface having an osteochondral defect 222
Place a guide pin through the guide feature of the guide and through the osteochondral defect into an underlying bone substrate 235
Using a cannulated cutter guided by the guide pin, create a socket by removing the cartilage defect, wherein the socket has an inner peripheral shape and a predetermined depth 240
Using an osteochondral graft that has an outer peripheral shape that corresponds to the inner peripheral shape and a length that is substantially transverse to the outer peripheral shape and substantially equal to the predetermined depth, insert the donor graft into the socket

FIG. 20

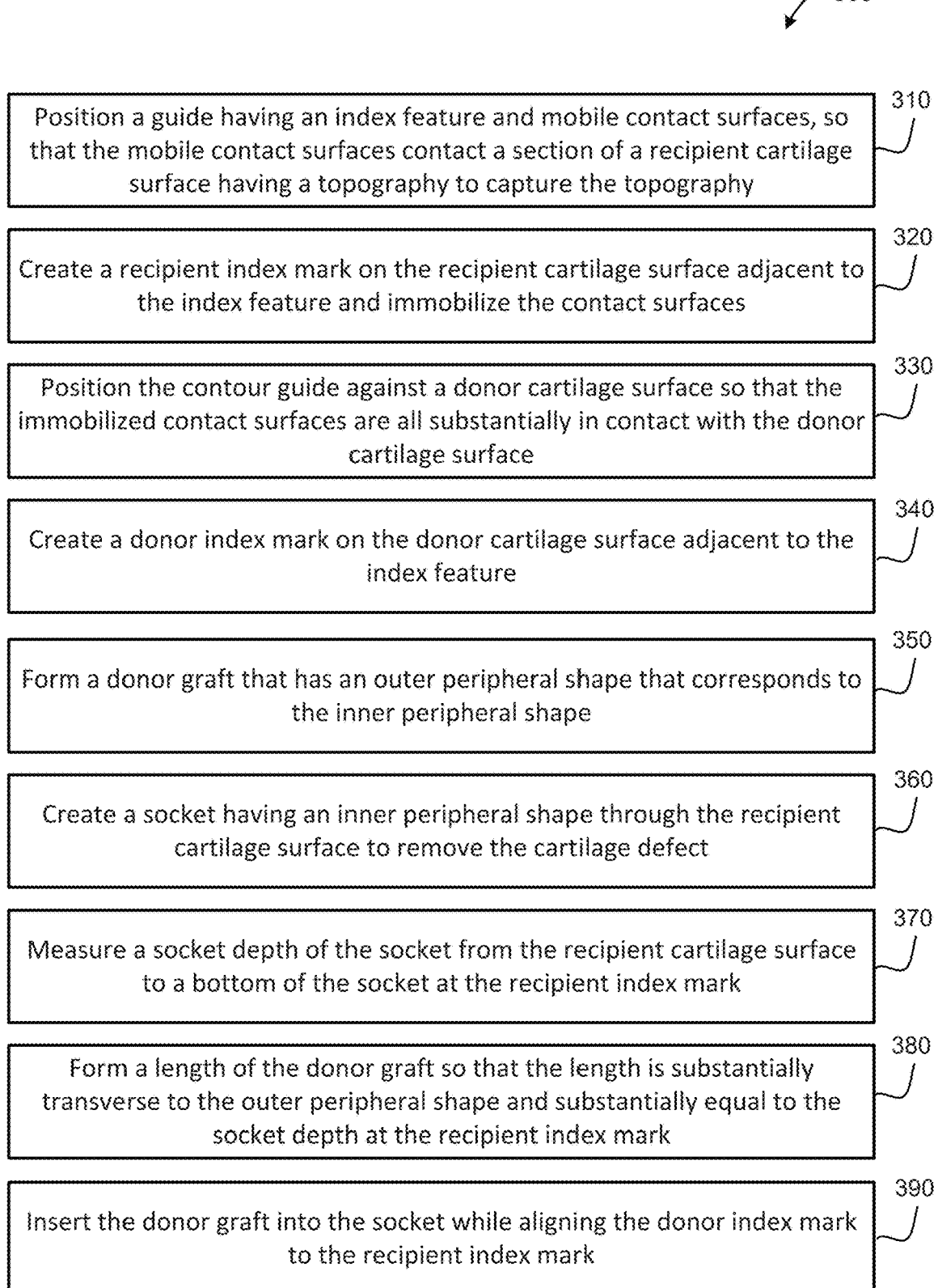

*300*

310
Position a guide having an index feature and mobile contact surfaces, so that the mobile contact surfaces contact a section of a recipient cartilage surface having a topography to capture the topography 320
Create a recipient index mark on the recipient cartilage surface adjacent to the index feature and immobilize the contact surfaces 330
Position the contour guide against a donor cartilage surface so that the immobilized contact surfaces are all substantially in contact with the donor cartilage surface 340
Create a donor index mark on the donor cartilage surface adjacent to the index feature 350
Form a donor graft that has an outer peripheral shape that corresponds to the inner peripheral shape 360
Create a socket having an inner peripheral shape through the recipient cartilage surface to remove the cartilage defect 370
Measure a socket depth of the socket from the recipient cartilage surface to a bottom of the socket at the recipient index mark 380
Form a length of the donor graft so that the length is substantially transverse to the outer peripheral shape and substantially equal to the socket depth at the recipient index mark 390
Insert the donor graft into the socket while aligning the donor index mark to the recipient index mark

FIG. 21

OSTEOCHONDRAL TRANSFER SYSTEMS AND METHODS

CROSS-REFERENCE TO RELATED APPLICATIONS

This application claims the benefit of U.S. Provisional Application Ser. No. 63/819,378, filed Jun. 6, 2025 and entitled OSTEOCHONDRAL TRANSFER SYSTEMS AND METHODS, which is incorporated by reference as though set forth herein in its entirety.

TECHNICAL FIELD

The present disclosure relates to the field of systems, methods, and devices for preparing and/or delivering osteochondral grafts.

BACKGROUND

Systems, devices, and/or methods for preparing and/or delivering osteochondral grafts are known in the art. However, known systems are unable to provide the level of geometrical precision or geometrical complexity desirable for osteochondral grafts used to restore and replicate the normal, complex, three-dimensional surface anatomy of cartilage at a graft recipient site. Thus, there is a need for an improved system, device, and/or method for preparing and/or delivering osteochondral grafts with geometrical features, such as area, length, cartilage surface contour, and cartilage surface orientation reference, that more closely match those of the recipient site. Finally, there is a need for improved systems, devices, and/or methods for preparing and/or delivering osteochondral grafts from cylindrical plugs or from bulk material made of autograft, allograft, xenograft, other biological materials, synthetic materials, or combinations thereof.

SUMMARY

According to one embodiment, a system may be provided for osteochondral defect repair. The system may include a guide with a first leg, a second leg, a third leg, a fourth leg, and a guide feature. The first leg, the second leg, the third leg, and the fourth leg may each have a distal tip. The distal tips of the first leg, the second leg, the third leg, and the fourth leg may lie in a plane. The guide feature may be oriented to define a working axis, perpendicular to the plane, along which a cutter is movable to remove bone and cartilage from a first bone.

In the system of any preceding paragraph, the guide feature may be a cannulation passing through the guide. The cannulation may be parallel to the working axis and may be configured to guide a pin along the working axis. The cannulation may further be sized to receive the pin with a close sliding fit.

In the system of any preceding paragraph, the system may further include the cutter. The cutter may be a trephine configured to be guided by the pin along the working axis.

In the system of any preceding paragraph, the first bone may be a recipient bone, and the trephine may be configured to remove a section of the recipient bone containing an osteochondral defect and to leave a socket suitable for receiving an osteochondral graft.

In the system of any preceding paragraph, the system may further include a cutting guide configured to receive an osteochondral graft. The cutting guide may be configured to guide further cutting of the osteochondral graft.

In the system of any preceding paragraph, the cutting guide may have an aperture configured to receive the osteochondral graft, and a distal surface configured to guide a saw blade to cut the osteochondral graft to a desired length that matches a depth of a socket formed in a recipient bone from removal of a section of the recipient bone containing an osteochondral defect.

In the system of any preceding paragraph, the system may further include an inserter configured to receive the osteochondral graft and deliver the osteochondral graft to the socket. The inserter may be configured to mate with the cutting guide such that the inserter receives the osteochondral graft as the osteochondral graft is inserted into the aperture.

In the system of any preceding paragraph, the system may further include an inserter and a plunger. The inserter may be configured to receive an osteochondral graft. The plunger may be configured to push the osteochondral graft out of the inserter and deposit the osteochondral graft into a socket formed in a recipient bone from removal of a section of the recipient bone containing an osteochondral defect.

In the system of any preceding paragraph, the system may further include the cutter. The cutter may be a trephine. The guide feature may have a cannulation passing through the guide. The cannulation may be sized to receive the trephine with a close sliding fit.

According to one embodiment, a system for osteochondral defect repair may include a cutter configured to slide along a pin to remove bone and cartilage from a first bone, and a guide configured to guide placement of the pin. The guide may include a first leg, a second leg, a third leg, a fourth leg, and a guide feature. The first leg, the second leg, the third leg, and the fourth leg may each have a distal tip. The distal tips of the first leg, the second leg, the third leg, and the fourth leg may lie in a plane. The guide feature may be oriented to guide placement of the pin along a working axis perpendicular to the plane.

In the system of any preceding paragraph, the guide feature may have a cannulation passing through the guide. The cannulation may be parallel to the working axis and may be configured to guide the pin along the working axis. The cannulation may be sized to receive the pin with a close sliding fit.

In the system of any preceding paragraph, the system may further include the pin. The cutter may be a trephine, and the pin may be configured to guide motion of the trephine along the working axis.

In the system of any preceding paragraph, the first bone may be a recipient bone, and the trephine may be configured to remove a section of the recipient bone containing an osteochondral defect and to leave a socket suitable for receiving an osteochondral graft.

In the system of any preceding paragraph, the system may further include a cutting guide configured to receive an osteochondral graft. The cutting guide may be configured to guide further cutting of the osteochondral graft.

In the system of any preceding paragraph, the cutting guide may have an aperture configured to receive the osteochondral graft, and a distal surface configured to guide a saw blade to cut the osteochondral graft to a desired length that matches a depth of a socket formed in a recipient bone from removal of a section of the recipient bone containing an osteochondral defect.

In the system of any preceding paragraph, the system may further include an inserter configured to receive the osteochondral graft and deliver the osteochondral graft to the socket. The inserter may be configured to mate with the cutting guide such that the inserter receives the osteochondral graft as the osteochondral graft may be inserted into the aperture.

In the system of any preceding paragraph, the system may further include an inserter and a plunger. The inserter may be configured to receive an osteochondral graft, and the plunger may be configured to push the osteochondral graft out of the inserter and deposit the osteochondral graft into a socket formed in a recipient bone from removal of a section of the recipient bone containing an osteochondral defect.

According to one embodiment, a method of repairing an osteochondral defect may include positioning a guide having four distal tips over a cartilage surface so that the four distal tips are positioned about a periphery of a section of the cartilage surface on a first bone, placing the guide so that three of the distal tips are in contact with the cartilage surface, rotating the guide until all four of the distal tips are in contact with the cartilage surface, and using the guide to guide a cutter to remove the section from the first bone.

In the method of any preceding paragraph, the four distal tips may be positioned on an end of each of four legs, the four distal tips may define a plane, and rotating the guide may include positioning the plane parallel to the section of the cartilage surface.

In the method of any preceding paragraph, using the guide to guide the cutter may include guiding the cutter along a working axis perpendicular to the section of the cartilage surface.

In the method of any preceding paragraph, using the guide to guide the cutter may include using the guide to guide insertion of a pin along the working axis into the first bone, and using the pin to guide the cutter along the working axis to remove the section.

In the method of any preceding paragraph, the first bone may be a recipient bone, and removing the section may include removing the osteochondral defect to leave a socket suitable for receiving an osteochondral graft.

In the method of any preceding paragraph, the method may further include Inserting the osteochondral graft into a cutting guide, and using the cutting guide to cut the osteochondral graft to fit the socket.

In the method of any preceding paragraph, the cutting guide may have an aperture and a distal surface. Inserting the osteochondral graft into the cutting guide may include inserting the osteochondral graft into the aperture, and cutting the osteochondral graft may include guiding a saw blade along the distal surface to cut the osteochondral graft to a desired length that matches a depth of the socket.

In the method of any preceding paragraph, the method may further include mating the cutting guide with an inserter such that the inserter receives the osteochondral graft as the osteochondral graft may be inserted into the aperture, and using the inserter to insert the osteochondral graft into the socket.

In the method of any preceding paragraph, the method may further include inserting an osteochondral graft into an inserter, and using a plunger to urge the osteochondral graft out of the inserter and into a socket formed in a recipient bone from removal of the section of the recipient bone containing the osteochondral defect.

According to one embodiment, a system for osteochondral defect repair may include a guide configured to determine a topography of a section of a cartilage surface of a first bone. The guide may include a body, a plurality of legs extending from the body, and a locking mechanism. The locking mechanism may be movable, without application of force along a working axis generally perpendicular to the cartilage surface, between an unlocked configuration, in which each of the legs are slidable, relative to the body, along the working axis to contact the cartilage surface to capture the topography, and a locked configuration, in which the locking mechanism engages the legs to prevent sliding of the legs, relative to the body, along the working axis.

In the system of any preceding paragraph, one of the plurality of legs may have an index pin, and one of the body and the index pin may have a marking designating the index pin.

In the system of any preceding paragraph, the locking mechanism may have a knob that is rotatable to move the locking mechanism between the unlocked configuration and the locked configuration.

In the system of any preceding paragraph, the locking mechanism may further have a lock ring with a plurality of arms configured to flex outward, in response to rotation of the knob, into frictional engagement with the legs.

In the system of any preceding paragraph, the system may further include a trephine, and a guide bushing with an aperture sized to receive either of the trephine and the guide in a close sliding fit.

In the system of any preceding paragraph, the guide bushing may have a plurality of fixation pin holes configured to receive fixation pins that secure the guide bushing to a second bone.

In the system of any preceding paragraph, the system may further include a plunger with a depth gauge, insertable into a socket in the first bone formed by removal of the section from the first bone, to indicate a depth of the socket.

In the system of any preceding paragraph, the system may further include an inserter configured to receive an osteochondral graft shaped to be received in the socket. The inserter may be further shaped to receive the plunger such that the plunger may be actuatable to urge the osteochondral graft out of the inserter and into the socket.

In the system of any preceding paragraph, the system may further include an inserter configured to receive an osteochondral graft and deliver the osteochondral graft to a socket in the first bone formed by removal of the section from the first bone, and a cutting guide configured to mate with the inserter to guide cutting of the osteochondral graft to a length that matches a depth of the socket.

In the system of any preceding paragraph, the system may further include a trephine configured to remove the section. In the unlocked configuration, each of the legs may be slidable, relative to the body, along the working axis to contact the section.

According to one embodiment, a system for osteochondral defect repair may include a cutter and a guide configured to determine a topography of a section of a cartilage surface of a first bone. The guide may include a body and a plurality of legs. The section may be defined by a perimeter between the section and surrounding cartilage. The cutter may include one of a trephine, a drill, and a punch sized to remove the section. The legs may be slidably movable relative to the body into contact with one of the section and the perimeter to capture the topography.

In the system of any preceding paragraph, one of the plurality of legs may include an index pin, and one of the body and the index pin may include a marking designating the index pin.

In the system of any preceding paragraph, the system may further include a locking mechanism with a knob that is rotatable to move the locking mechanism between an unlocked configuration, in which each of the legs is slidable, relative to the body, along a working axis of the guide to contact the cartilage surface to capture the topography, and a locked configuration, in which the locking mechanism engages the legs to prevent sliding of the legs, relative to the body, along the working axis.

In the system of any preceding paragraph, the locking mechanism may further include a lock ring may include a plurality of arms configured to flex toward the legs, in response to rotation of the knob, into frictional engagement with the legs.

In the system of any preceding paragraph, the system may further include a guide bushing with an aperture sized to receive the cutter and the guide in a close sliding fit.

In the system of any preceding paragraph, the guide bushing may include a plurality of fixation pin holes configured to receive fixation pins that secure the guide bushing to a second bone.

In the system of any preceding paragraph, the system may further include a plunger with a depth gauge, insertable into a socket in the first bone formed by removal of the section from the first bone, to indicate a depth of the socket.

In the system of any preceding paragraph, the system may further include an inserter configured to receive an osteochondral graft shaped to be received in the socket. The inserter may be further shaped to receive the plunger such that the plunger is actuatable to urge the osteochondral graft out of the inserter and into the socket.

In the system of any preceding paragraph, the system may further include an inserter configured to receive an osteochondral graft and deliver the osteochondral graft to a socket in the first bone formed by removal of the section from the first bone, and a cutting guide configured to mate with the inserter to guide cutting of the osteochondral graft to a length that matches a depth of the socket.

According to one embodiment, a system for osteochondral defect repair may include a cutter, a guide bushing with an interior surface, and a guide. The guide may include a body defining a longitudinal axis, the body having an exterior surface, a plurality of legs, and a locking mechanism. The locking mechanism may be movable between an unlocked configuration, in which each of the legs is slidable, relative to the body, along the longitudinal axis to contact a first cartilage surface of a first bone to capture a topography of a first section of the first cartilage surface, and a locked configuration, in which the locking mechanism engages the legs to prevent sliding of the legs, relative to the body, along the longitudinal axis. The exterior surface of the guide may be configured to engage the interior surface of the guide bushing to guide placement of the guide bushing, and engage the cutter to guide motion of the cutter to remove a second section, sized to replace the first section, from a second cartilage surface of a second bone.

In the system of any preceding paragraph, one of the plurality of legs may include an index pin, and one of the body and the index pin may include a marking designating the index pin.

In the system of any preceding paragraph, the locking mechanism may include a knob that is rotatable to move the locking mechanism between the unlocked configuration and the locked configuration, and a lock ring with a plurality of arms configured to flex toward the legs, in response to rotation of the knob, into frictional engagement with the legs.

In the system of any preceding paragraph, the interior surface of the guide bushing may include an aperture sized to receive the cutter and the guide in a close sliding fit.

In the system of any preceding paragraph, the guide bushing may include a plurality of fixation pin holes configured to receive fixation pins that secure the guide bushing to the second bone.

In the system of any preceding paragraph, the system may further include a plunger and an inserter configured to receive the second section. The inserter may be further shaped to receive the plunger such that the plunger is actuatable to urge the second section out of the inserter and into a socket defined by removing the first section from the first bone.

In the system of any preceding paragraph, the system may further include an inserter configured to receive the second section and deliver the second section to a socket defined by removing the first section from the first bone, and a cutting guide configured to mate with the inserter to guide cutting of the second section to a length that matches a depth of the socket.

According to one embodiment, a method for osteochondral defect repair may include positioning a guide over a first cartilage surface of a first bone. The guide may include a body with an exterior surface, and a plurality of legs, each of which includes a distal tip. The method may further include sliding the legs relative to the body so that each of the distal tips is in contact with the first cartilage surface, locking the legs to prevent further sliding of the legs relative to the body to capture a topography of a first section, placing the distal tips in contact with a second cartilage surface of a second bone, using the body to guide placement of a guide bushing over the second bone, securing the guide bushing to the second bone, and using the guide bushing to guide motion of a cutter to remove a second section of the second cartilage surface.

In the method of any preceding paragraph, the method may further include removing the first section from the first bone to define a socket in the first bone, and Inserting the second section into the socket.

In the method of any preceding paragraph, inserting the second section into the socket may include, with an inserter, receiving the second section, and actuating a plunger into the inserter to urge the second section out of the inserter and into the socket.

In the method of any preceding paragraph, the method may further include mating a cutting guide with the inserter, and using the cutting guide to guide cutting of the second section to a length that matches a depth of the socket.

In the method of any preceding paragraph, sliding the legs relative to the body may include sliding the legs along a longitudinal axis defined by the body, and locking the legs may include locking the legs without exerting significant force on the guide along the longitudinal axis.

In the method of any preceding paragraph, the guide bushing may include a plurality of fixation pin holes, and securing the guide bushing to the second bone may include inserting a plurality of fixation pins through the fixation pin holes and into the second bone.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which:

FIG. 1 is a perspective view of a 3-legged pin guide according to one embodiment.

FIG. 2 is a perspective view of a 4-legged pin guide according to one embodiment.

FIG. 3A is a top view of a cylindrical cartilage surface showing the 3-legged pin guide of FIG. 1 in a first position.

FIG. 3B is a front elevation view of the items shown in FIG. 3A.

FIG. 3C is a top view of a cylindrical cartilage surface showing a 3-legged pin guide of FIG. 1 in a second position.

FIG. 3D is a front elevation of the items shown in FIG. 3C.

FIG. 6 is a perspective view of the guide and pin of FIG. 5, and a distal femur.

FIG. 7A is a perspective view of the pin and cannulated cutter of FIG. 5, and the distal femur.

FIG. 7B is a perspective view of the distal femur of FIG. 7A.

FIG. 17A is a front elevation, exploded view of the base, inserter, and cutting guide of FIG. 12, and the osteochondral graft of FIG. 16B.

FIG. 17B is a front elevation, section, assembled view of the items shown in FIG. 17A.

FIG. 17C is a front elevation section view of the items shown in FIG. 17A, after the osteochondral graft is trimmed to a desired length.

FIG. 18A is a perspective view of the osteochondral graft of FIG. 16B and the inserter and plunger of FIG. 12, and the distal femur.

FIG. 18B is a perspective view of the osteochondral graft of FIG. 16B, and the distal femur.

FIG. 20 is a flowchart depicting an osteochondral repair method suitable for use with the surgical kit of FIG. 5, according to an embodiment.

FIG. 21 is a flowchart depicting an osteochondral repair method suitable for use with the surgical kit of FIG. 12, according to an embodiment.

Figure 4A:
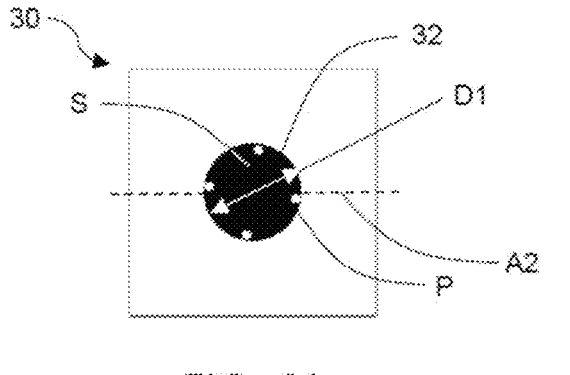
FIG. 4A is a top view of a cylindrical cartilage surface showing the 4-legged pin guide of FIG. 2 in a first position.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

To reconstruct a cartilage surface of diseased or damaged cartilage and underlying bone (called an osteochondral defect or osteochondral lesion), it is desirable to reproduce the cartilage surface topography at the reconstruction site (called a recipient site) by producing an osteochondral graft taken from a donor site with matching cartilage surface topography. Many osteochondral lesions may be circumscribed by a circular perimeter having a defect diameter. Thus, a cylindrical socket that matches the defect diameter may be formed with a cutting tool at the recipient site, an osteochondral graft cylindrical plug that matches the defect diameter may be formed with a cutting tool at a donor site, and the osteochondral graft plug may be taken from the donor site, transferred, and implanted at the recipient site. Alternatively, the osteochondral graft plug may be premade and properly shaped from constituent parts. The osteochondral graft plug may include autograph, allograph, xenograft, other biological materials, synthetic materials, and/or combinations thereof. As used herein, "osteochondral graft" or "graft" also refers to a graft made only of cartilage, which may be used in cases where the bone underlying diseased or damaged cartilage remains healthy.

Continuity at the margin between a donor graft cartilage surface and a recipient site cartilage surface is desired, since cartilage surface mismatch at the graft-host interface can lead to pain, cartilage wear, and graft dislodgement. Thus, careful determination of the trajectory (i.e., "working axis") of a socket relative to adjacent cartilage at a recipient site and/or the angle between a top cartilage surface and sidewalls of a donor osteochondral graft are desired to ensure that cartilage surface mismatch is avoided. For the purposes of the discussion below, it is assumed that the desired angle between a top cartilage surface (or for an uneven cartilage surface, the plane that most closely approximates the top cartilage surface) and sidewalls of a donor osteochondral graft is 90 degrees. Thus, the desired trajectory of a socket relative to adjacent cartilage at a recipient site is also 90 degrees, or perpendicular to the cartilage surface.

To create a socket at a graft recipient site, a guide pin may be placed centrally into bone underlying an osteochondral defect, and a cannulated cutting tool may be positioned over the guide pin and advanced toward the bone to create the socket. Thus, careful determination of the trajectory of the guide pin is important to ensure that the socket is properly oriented relative to the surface of the cartilage at the recipient site. A hollow cylindrical device (herein called a "pin guide" or "guide") with a flat distal rim at the end may be used for this purpose. Some pin guides may have an inner diameter that provides a close sliding fit with a guide pin, a concave distal end to accommodate cartilage convexity, and a planar distal rim that circumscribes the osteochondral defect. However, since most cartilage surfaces have complex curvature, it can be difficult to ensure that the planar distal rim lies parallel to the cartilage surface, as the planar distal rim can be tangent anywhere along the curvature of the cartilage surface. To improve upon this, a pin guide with three discrete flat surfaces on its distal end could alternatively be used, but this design also has limitations in that three points of contact may not be sufficient to locate the working axis with reliable perpendicularity to the cartilage surface, as will be set forth in more detail below.

To achieve cartilage topography matching with an osteochondral graft transfer technique, four geometric parameters may be considered regarding the cylindrical form of the plug and recipient site: diameter, length, longitudinal axis (or working axis) trajectory, and radial position (clocking). It is desirable to have a trialing technique that produces a unique combination (i.e., a single solution) of all four of these geometric parameters at a recipient site, so that this unique combination can be reproduced at an osteochondral plug harvest site to create a plug that is an accurate match when transferred and implanted into the recipient site socket.

FIG. 1 shows a guide, according to one embodiment, which may take the form of a pin guide 10. The pin guide 10 may be used to guide a pin along a working axis, representing a desired trajectory for future cutting steps relative to a recipient bone and/or a donor bone. In alternative embodiments, rather than guiding a pin, a guide may directly guide motion of the cutter along the working axis. In this application, "working axis" is based on the desired trajectory of a cutter and/or osteochondral graft, while "longitudinal axis" relates to the line extending along the longest length of an object such as a guide. The longitudinal axis may extend along the greatest length of the object, or the axis of radial symmetry or approximate radial symmetry. These terms are not synonymous, but when the object is placed in alignment with the trajectory, the longitudinal axis of an instrument will be positioned coaxially with the working axis of the associated graft repair or harvesting site. Thus, they may, in some instances, be used interchangeably.

The pin guide 10 may have 3 legs having rounded distal tips. In this application, "leg" refers to any protrusion with a tip capable of making contact with a cartilage or bone surface. A leg need not have any particular aspect ratio. The 3-legged pin guide 10 may represent an improvement over the prior art devices that have 3 distal flats. Rounded distal tips can be advantageous over flat distal tips since rounded distal tips, when in contact with cartilage, will make point contact at a known location, which will always be very close to a central axis of a leg. A leg having a flat surface on its distal end, when in contact with cartilage, may make point contact anywhere within the area of the flat surface, resulting in a less predictable contact location.

FIG. 2 shows a guide, according to one embodiment, which may take the form of a pin guide 20. The pin guide 20 may have 4 legs.

Pin guides 10 and pin guide 20 may each have a body 12 with an elongated body having a longitudinal axis A1, and the body 12 may further have a central cannulation 18 that extends along longitudinal axis A1. The body 12 may have legs 14 that extend distally from the body 12 and parallel to longitudinal axis A1. The legs 14 have distal tips 16 that may be positioned an equal radial distance from longitudinal axis A1 such that the distal tips 16 lie within a circle having a diameter D1. Further, the distal tips 16 may all lie in a plane 15 that is perpendicular to longitudinal axis A1. Each of the legs 14 have a length as measured from the body 12 to the distal tips 16, and each of the legs 14 also have a width. The aspect ratio of the length to width of each of the legs 14 may be greater than 1. More precisely, the aspect ratio may be between 2 and 20. Yet more precisely, the aspect ratio may be between 5 and 15. Still more precisely, the aspect ratio may be between 8 and 12. In some embodiments, the aspect ratio may be about 10.

By way of an example, a cartilage surface may be reconstructed such that it conforms to a portion of a cylindrical surface 30 having a diameter D2 and a longitudinal axis A2 as shown in FIGS. 3A through 4D. The cartilage surface 30 may have a defect that is circumscribed by a circle 32 having diameter D1. The circle 32 may define a section S of cylindrical surface 30 that is to be replaced. Projecting a circle with diameter D1 along an axis that is perpendicular to longitudinal axis A2, an intersection is created at a perimeter P. Section S is bounded by perimeter P, and has a radius of curvature equal to D2 divided by 2.

The 3-legged pin guide 10 of FIG. 1 may be used to place a guide pin centrally through section S (the cartilage surface) and into the underlying bone, so that the guide pin may guide a cannulated cutting tool along longitudinal axis A1 to form a socket with a diameter D1 for receiving an osteochondral graft plug having a diameter D1. A first distal tip 16 of a first leg 14 of the 3-legged pin guide 10 may be placed at any arbitrary first contact point along perimeter P. Then a second distal 16 tip of a second leg 14 of the 3-legged pin guide 10 may be placed at a second contact point that is 120 degrees to the first distal tip on perimeter P. First and second contact points define an axis about which the 3-legged pin guide 10 may be rotated until third distal tip 16 contacts perimeter P at a third contact point.

With all distal tips 16 of all 3 legs 14 of the 3-legged pin guide 10 in contact with perimeter P, the 3-legged pin guide 10 is "fully registered" with section S. However, since the first contact point was at an arbitrary location, there are an infinite number of radial clocking registrations between the 3-legged pin guide 10 and the section S. For example, if first contact point is at the farthest right location of perimeter P as shown in FIGS. 3A and 3B, then when full registration is achieved, the longitudinal axis A1 of pin guide 10 will be at an acute angle relative to the left end of longitudinal axis A2 as shown in FIG. 3B. But if the first contact point is at the farthest left location of perimeter P as shown in FIGS. 3C and 3D, then when full registration is achieved, the longitudinal axis A1 of pin guide 10 will be at an obtuse angle relative to the left end of longitudinal axis A2 as shown in FIG. 3D. Thus, longitudinal axis A1 is never perpendicular to longitudinal axis A2, and the 3-legged pin guide 10 fails to provide a reliable and predictable working axis trajectory or radial position (clocking) to ensure the harvest, transfer and implantation of an osteochondral plug will accurately reproduce the native cartilage surface topography.

However, registration of the 4-legged pin guide 20 in FIG. 2 to section S may yield a surprising result. Using a similar sequence of steps as described above, a first distal tip 16 of a first leg 14 of the 4-legged pin guide 20 may be placed at any arbitrary first contact point along perimeter P. Then a second distal tip 16 of a second leg 14 of the 4-legged pin guide 20 may be placed at a second contact point that is 90 degrees to the first distal tip on perimeter P. First and second contact points define an axis about which 4-legged pin guide 20 may be rotated until a third distal tip 16 contacts perimeter P at a third contact point. However, the fourth distal tip 16 may not be in contact with perimeter P when the other three distal tips 16 are in contact with perimeter P as shown in FIGS. 4A and 4B. Contact of the fourth distal tip 16 may be checked by attempting to rotate the 4-legged pin guide 20 about an axis passing through the first and third points (called the "y-axis check"-essentially checking for whether the pin guide 20 is able to wobble on the cartilage surface). If motion is detectable, the fourth distal tip is not in contact with perimeter P.

Figure 4C:
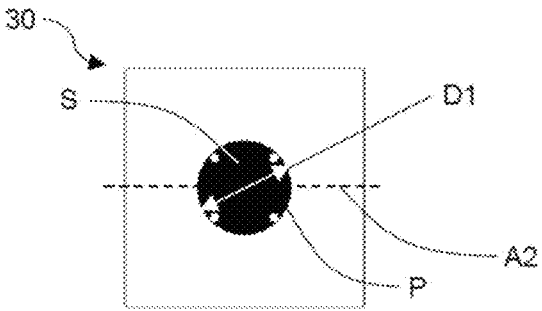
FIG. 4C is a top view of a cylindrical cartilage surface showing the 4-legged pin guide of FIG. 2 in a second position.
Figure 4B:
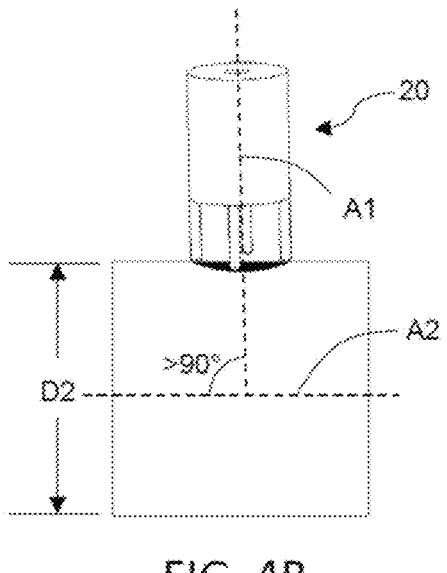
FIG. 4B is a front elevation of the items shown in FIG. 4A.
Figure 4D:
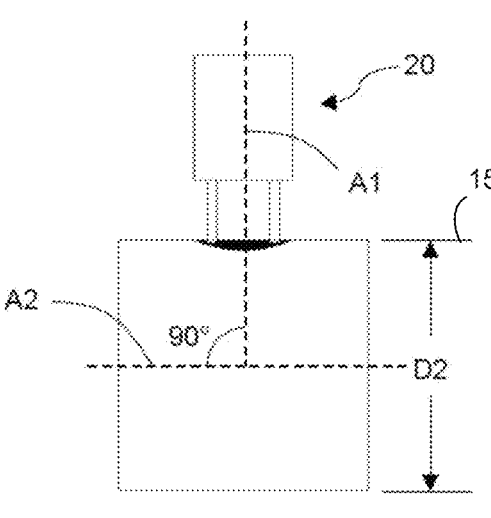
FIG. 4D is a front elevation view of the items shown in FIG. 4C.

By rotating the 4-legged pin guide 20 about its longitudinal axis A1 and repeating the y-axis check, there will be one and only one clocking position within a 90-degree arc at which the y-axis check will result in no detectable motion (or wobble), indicating all four distal tips 16 are in contact with perimeter P as shown in FIGS. 4C and 4D. Due to the 90-degree rotational symmetry of the 4-legged pin guide 20, there will be four rotational positions of the 4-legged pin guide 20 where all four distal tips are in contact with perimeter P.

Following a successful y-axis check, an attempt to rotate the 4-legged pin guide 20 about the second and fourth contact points (called the "x-axis check") can optionally be used to confirm that the first and third points are still in contact. Furthermore, when all four distal tips are in contact with perimeter P as shown in FIGS. 4C and 4D, longitudinal axis A1 will be perpendicular to longitudinal axis A2, thus defining the desired working axis. Thus, the 4-legged pin guide 20 provides users with a fast and repeatable method to define a unique working axis and radial position (clocking) to ensure the harvest, transfer and implantation of an osteochondral graft plug along the associated trajectory will accurately align with the native cartilage surface topography.

To facilitate clear visualization of the contact points, the legs 14 of the 4-legged pin guide 20 may have a higher aspect ratio as described above to ensure that the body 12 of the 4-legged pin guide 20 is spaced sufficiently away from the cartilage surface so that the body 12 does not contact section S nor obscure direct visualization of the four discrete contact points of the four distal tips 16. Visual confirmation of direct contact with the four distal tips 16 can be used in place of, or in addition to, the x-axis check and the y-axis check, to ensure proper registration of the pin guide to the cartilage surface.

The unique geometric registration position of the 4-legged pin guide 20 to section S is the location at which, when observed along longitudinal axis A1, an axis constructed between any two distal tips 16 of adjacent legs 14 of the 4-legged pin guide 20 are either parallel or perpendicular to longitudinal axis A2. Similar to the foregoing analysis, it can be shown that a unique registration position exists for the 4-legged pin guide 20 registered against other surface patch morphologies, including a conical surface, a parabolic surface, a toroidal surface, two adjacent surfaces of a polyhedron (surfaces that share a common edge), or any other surface with axial or planar symmetry. In the case of the polyhedron surfaces, the length of the common edge must be greater than or equal to the distance between two distal tips 16 of adjacent legs 14 of the 4-legged pin guide 20. The foregoing list of applicable surface geometries provides a highly accurate approximation of the surface geometries found in most articular joint cartilage surfaces in the mammalian body.

The 4-legged pin guide 20 may ensure that, at the four equally spaced contact points along a perimeter, the donor plug cartilage surface and the recipient site cartilage surface will be an exact match. However, the cartilage surface matching between contact points is not certain. For most small defects (e.g., approximately 6-14 mm in diameter) and for flatter cartilage surface topographies, the "worst case" lack of fidelity between contact points is minimal and is not clinically significant. However, for larger defects (e.g., greater than 14 mm in diameter), or defects with a more complex cartilage surface morphologies, more contact points may help to ensure clinically relevant fidelity of the reconstructed cartilage surface topography, as will be described subsequently.

Figure 5:
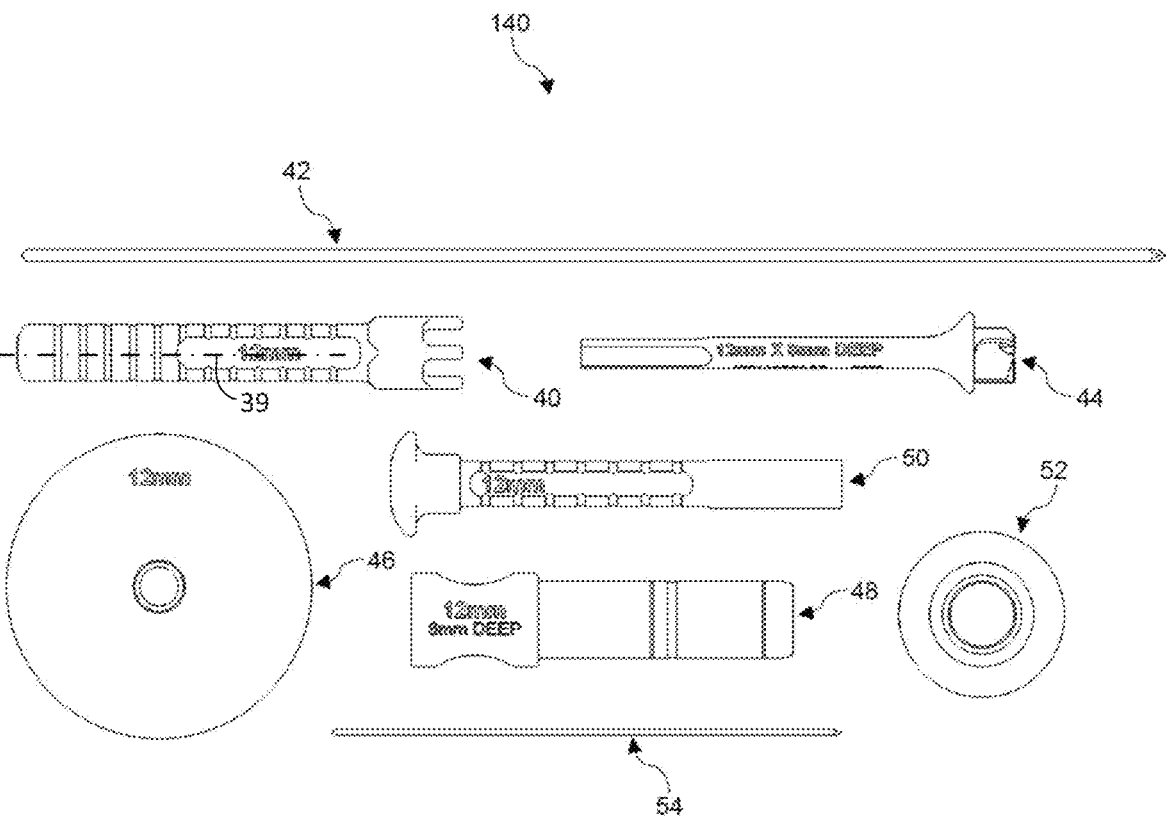
FIG. 5 is a top view of a surgical kit according to one embodiment.

FIG. 5 shows a surgical kit 140 and FIGS. 6 through 9B show a method for conducting an osteochondral transfer procedure using the surgical kit 140. The surgical kit 140 in FIG. 5 may include the following components: a pin, which may be a guide pin 42, a guide which may be a pin guide 40, a cutter, which may be a cannulated drill 44 (or a trephine having a larger cannulation), a plunger 50, an inserter 48, a cut guide 52, a base 46, and a K-wire 54. In this application, a "cutter" is any apparatus suitable for cutting bone and/or cartilage. A "rotary cutter" is a cutter designed to rotate about an axis as cutting occurs. A "trephine" is a rotary cutter with an interior bore suitable for receiving bone and/or cartilage. A "cut guide" or "cutting guide" is any object with one or more surfaces shaped and positioned to guide motion of a cutter.

As shown in FIG. 6, pin guide 40 may have a body 41, a guide feature which may be a cannulation 47 extending through body 41 along a longitudinal axis 39, of body 41, legs 43 extending distally from body 41, and distal tips 45 located on the distal end of legs 43. In this application, a "guide feature" is any object or surface that is shaped and aligned to guide another object along a defined trajectory. A guide feature may be fully-bounded, as in the case of a through hole, which may have a circular, polygonal, or other shape. In the alternative, a guide feature may be an exterior feature of an object, such as a trough or slot. The guide feature may advantageously have a shape that closely conforms to that of the object to be guided (for example, a circular through hole to guide placement of a pin with a circular cross-sectional shape. The guide feature may advantageously have a close sliding fit with the object to be guided.

FIG. 6 shows the pin guide 40 with all four distal tips 45 in contact with a cartilage surface 101 of a distal femur 100, and the guide pin 42 placed through cannulation 47 of the pin guide 40 and into cartilage surface 101 and underlying bone of distal femur 100. Cannulation 47 may receive guide pin 42 in a close sliding fit. In this application, a "close sliding fit" is a fit between male and female features that are relatively sized such that the male feature is able to slide with little resistance within the female feature, with a sufficiently tight fit to substantially maintain concentricity and/or coaxiality between the male and female features.

Distal tips 45 may contact the cartilage surface 101 within and/or at the edge of the section of cartilage surface 101 that is to be removed. This may advantageously provide more accurate perpendicularity, as compared with devices that register only on the cartilage, outside of the surface to be removed.

After removing the pin guide 40 from guide pin 42, the cannulated drill 44 may be placed over guide pin 42 and may be used to create a socket 102 as shown in FIGS. 7A and 7B having a diameter (DP, not shown) in the cartilage surface 101 and underlying bone at a predetermined depth (PD, not shown). The cannulated drill 44 may have depth marks (not shown) or it may have a physical shoulder 49 as shown to ensure that the socket depth is PD.

Figure 7C:
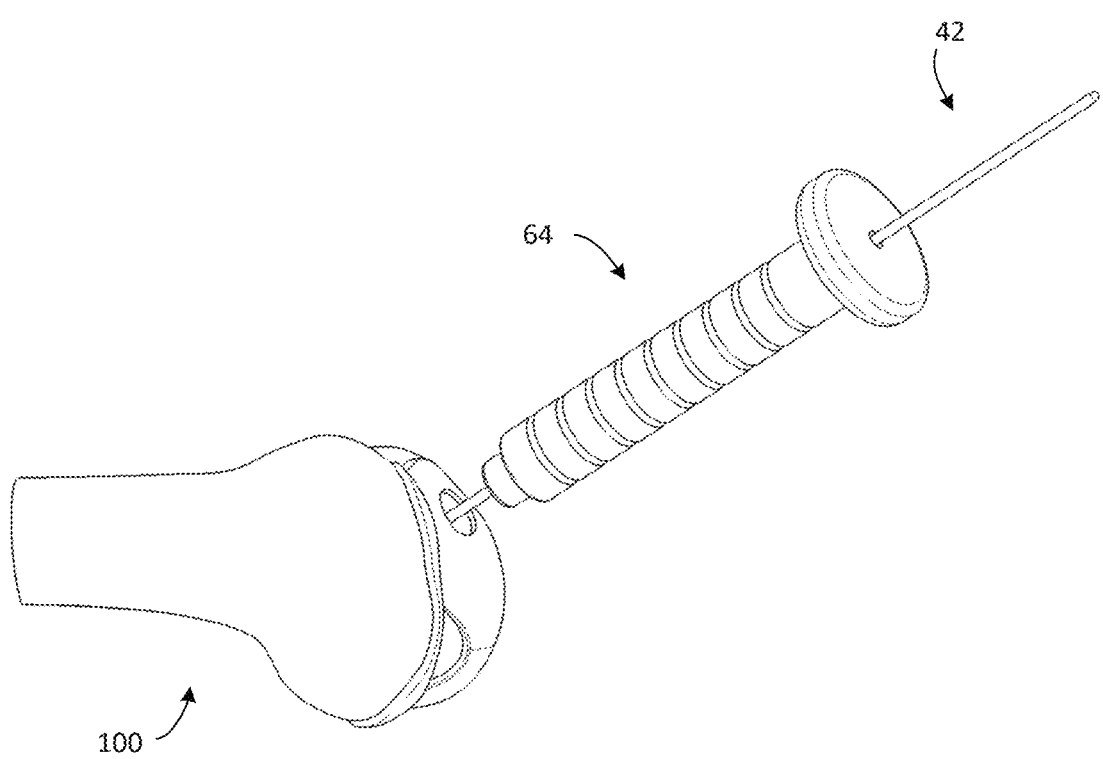
FIG. 7C is a perspective view of the pin of FIG. 5 with a punch.
Figure 7D:
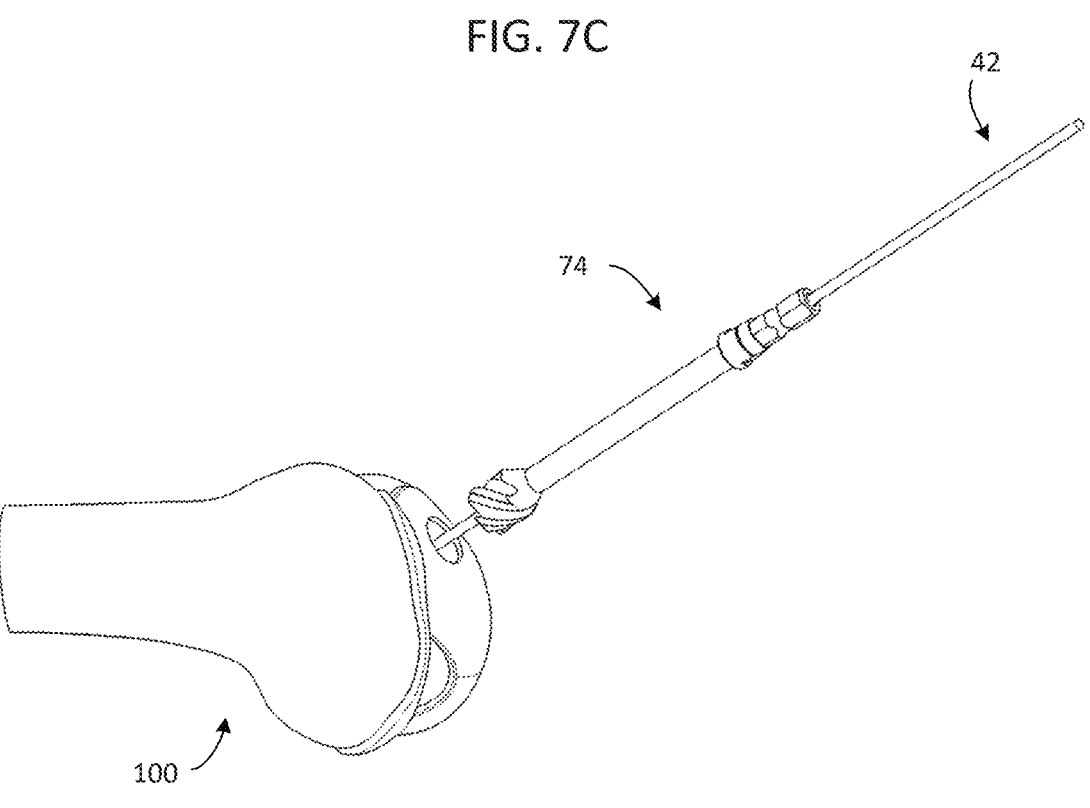
FIG. 7D is a perspective view of the pin of FIG. 5 with an alternative cannulated drill.

In alternative embodiments, other cutter types may be used in place of the cannulated drill 44. For example, as mentioned previously, a trephine may be used, and may be functionally similar to cannulated drill 44, but with a larger cannulation, for example, to preserve some of the removed bone and/or cartilage. As shown in FIGS. 7C and 7D, a punch 64 or an alternative cannulated drill 74 may be used. Like cannulated drill 44, punch 64 and alternative cannulated drill 74 may slide over guide pin 42 along longitudinal axis 39 to remove the desired bone and/or cartilage from distal femur 100. Alternative cannulated drill 74 may be rotated during insertion to cut with rotary action, like cannulated drill 44. Punch 64 may be impacted or otherwise driven into distal femur 100 to create an annular bore around the bone and/or cartilage to be removed. If desired, with any of the cutters set forth above, other instruments may then be used to remove the bone/cartilage plug from distal femur 100.

Figures 8A, 8B, 8C, 9A, 9B:
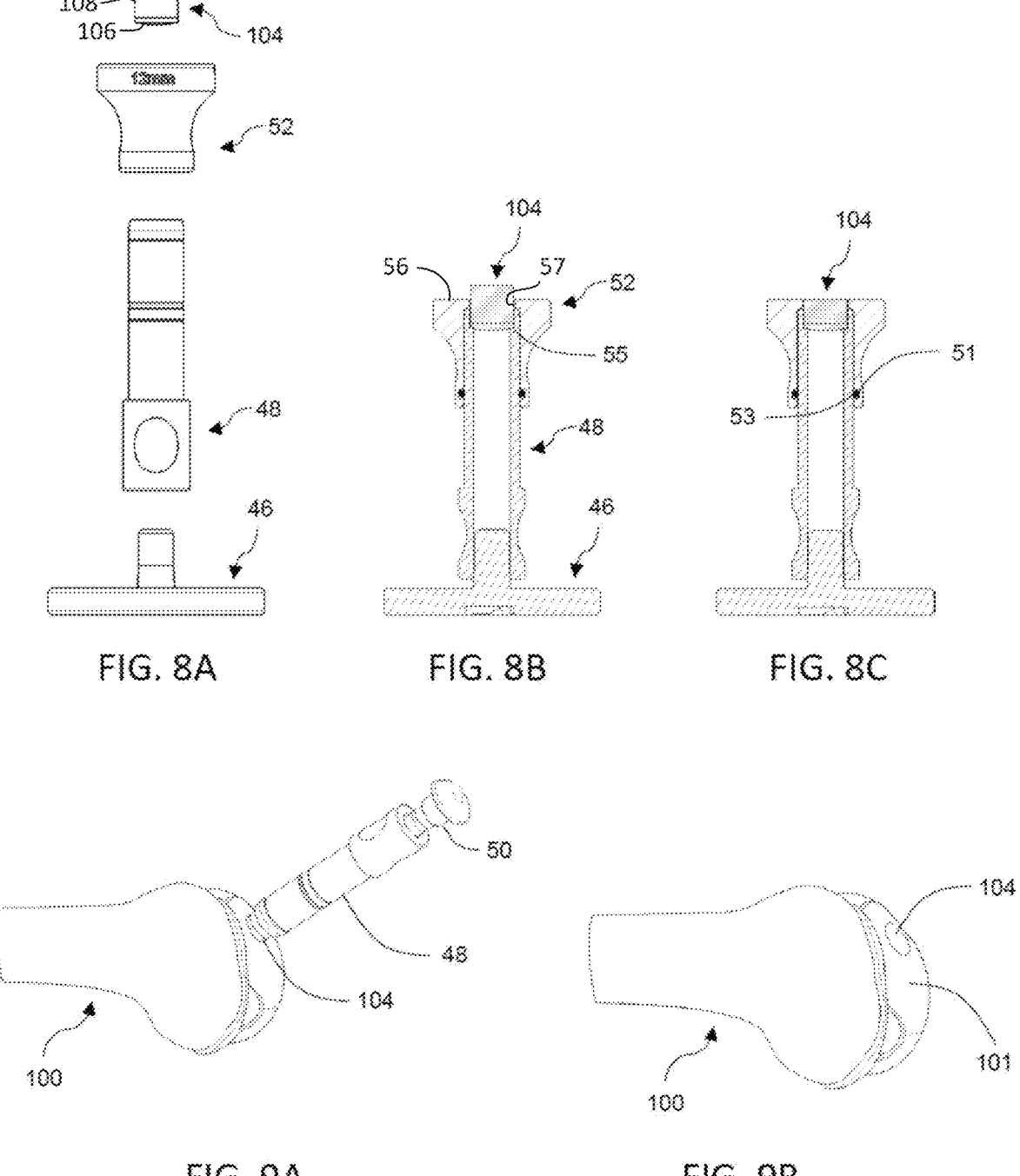
FIG. 8A is a front elevation, exploded view of the base, the inserter, and the cutting guide of FIG. 5, and an osteochondral graft.
FIG. 8B is a front elevation, section, assembled view of the items shown in FIG. 8A.
FIG. 8C is a front elevation, section, assembled view of the items shown in FIG. 8A after the osteochondral graft is trimmed to a desired length.
FIG. 9A is a perspective view of the osteochondral graft of FIG. 8A, the inserter and plunger of FIG. 5, and a distal femur.
FIG. 9B is a perspective view of the items shown in FIG. 9A.

Next, the inserter 48 may be connected to the base 46, and an osteochondral graft 104 having a cylindrical shape with diameter DP (or approximately DP) may be inserted into the distal end of the inserter 48 with a cartilage end of the osteochondral graft 104 positioned proximally as shown in FIGS. 8A, 8B, and 8C (the distal end of the inserter 48 is facing up and the proximal end of the inserter 48 is facing down in FIGS. 8A, 8B, and 8C). The osteochondral graft 104 may be seated against an internal shoulder 55 of the inserter 48 as shown in FIG. 8B, with the cartilage surface 106 of the osteochondral graft 104 abutting the internal shoulder 55. The bone substrate 108 of the osteochondral graft 104 may lie distal to the cartilage surface 106.

Then, the cut guide 52 may be installed onto the distal end of the inserter 48 until a resilient member 51 on the cut guide 52 engages a groove 53 externally located on the inserter 48 as shown in FIG. 8C. The interaction of the groove 53 and the resilient member 51 may provide tactile feedback indicating to the surgeon that the inserter 48 and cut guide 52 are properly coupled together and may prevent premature decoupling. Advantageously, the distance between the distal (top) surface of the cut guide 52 and the internal shoulder 55 of the inserter 48 may be equal to, or approximately equal to, PD.

In alternative embodiments, the resilient member 51 may be located on the inserter 48 and the groove 53 may be located on the cut guide 52. Alternatively, the resilient member 51 may be integral to either the inserter 48 or the cut guide 52. Alternatively, the cut guide 52 may be integral to the inserter 48. In yet other alternative embodiments, the cut guide 52 and the inserter 48 may be separate, but may be coupled and/or locked together through the use of other methods known in the art, such as clips, clamps, threading, and/or the like.

Returning to FIG. 8C, mating of the cut guide 52 with the inserter 48 may cause part of the osteochondral graft 104 to be received in an aperture 57 of the cut guide 52. A saw blade (not shown) may be then used to trim the length of the osteochondral graft 104 flush with the distal surface 56 of the cut guide 52, thus creating an osteochondral graft 104 having a length equal, or approximately equal, to PD. Optionally, a K-wire 54 may be placed through a hole (not shown) in the side of cut guide 52 and into the side of osteochondral graft 104 to secure the osteochondral graft 104 during the cutting operation.

Next, as shown in FIG. 9A, the cut guide 52 may be removed from the distal end of the inserter 48, and the plunger 50 may be inserted into the proximal end of the inserter 48. The distal end of the osteochondral graft 104 and inserter 48 may then be placed adjacent to the socket 102, and the plunger 50 may be used to expel the osteochondral graft 104 from the inserter 48 and into the socket 102 until a cartilage surface of the osteochondral graft 104 is flush with the surface of cartilage surface 101 surrounding the socket 102 as shown in FIG. 9B. Alternatively, the plunger 50 by be used to expel the osteochondral graft 104 from the inserter 48, and the osteochondral graft 104 may be placed into socket 102 by hand.

In some embodiments, the osteochondral graft 104 may be inserted without regard to the orientation of the osteochondral graft 104 about the insertion axis. The fact that the cartilage surface 106 of osteochondral graft 104 is substantially perpendicular to the socket 102 may cause the cartilage surface 106 of osteochondral graft 104 to lie substantially flush with the surrounding cartilage. Any surface discontinuities may be insufficient in size to affect articulation of the distal femur 100 with the associated tibia and/or patella.

However, in alternative embodiments, it may be desirable to insert osteochondral graft 104 at a predetermined orientation about the insertion axis. A surgeon may mark the cartilage surface of osteochondral graft 104 and/or the underlying bone with a marker such as a surgical pen. A corresponding marking may be made on distal femur 100, for example, on the cartilage surrounding the socket 102. Then, during insertion the marking on osteochondral graft 104 may be aligned with the marking on distal femur 100 to ensure that osteochondral graft 104 is inserted at the desired orientation relative to distal femur 100.

The osteochondral graft 104 may be readily sourced from a tissue bank. It is known in the art that tissue banks provide osteochondral grafts in the form of a cylinder having a longitudinal axis, a predetermined diameter, and a length. The cylinder may further have a generally flat cartilage top surface and a generally flat bone bottom surface, and these surfaces may be generally perpendicular to the longitudinal axis of the cylinder. Alternatively, osteochondral graft 104 may be harvested from a larger graft, as discussed below in relation to FIGS. 19A and 19B.

As mentioned above, a guide may advantageously have more contact points to ensure clinically relevant fidelity of the reconstructed cartilage surface topography for osteochondral defects that are large or that have complex cartilage surface morphology. One exemplary guide with additional contact points will be shown and described in connection with FIGS. 10 through 16B.

Figure 10:
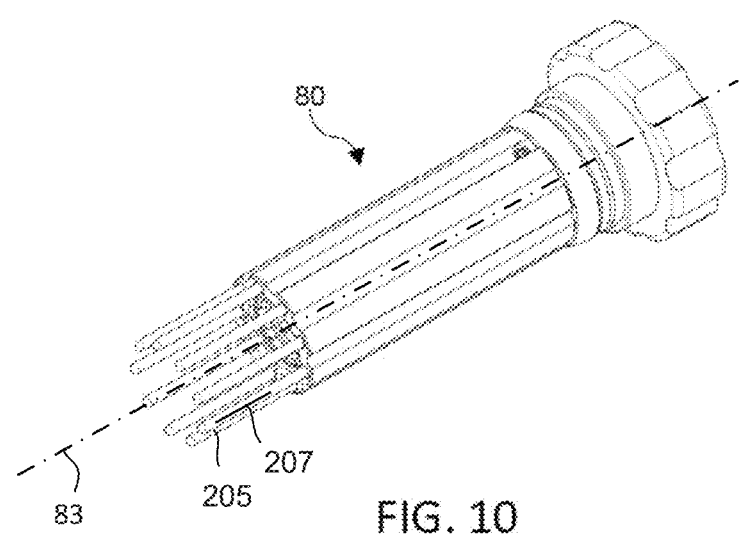
FIG. 10 is a perspective view of a contour guide in an assembled state, according to one embodiment.
Figure 11:
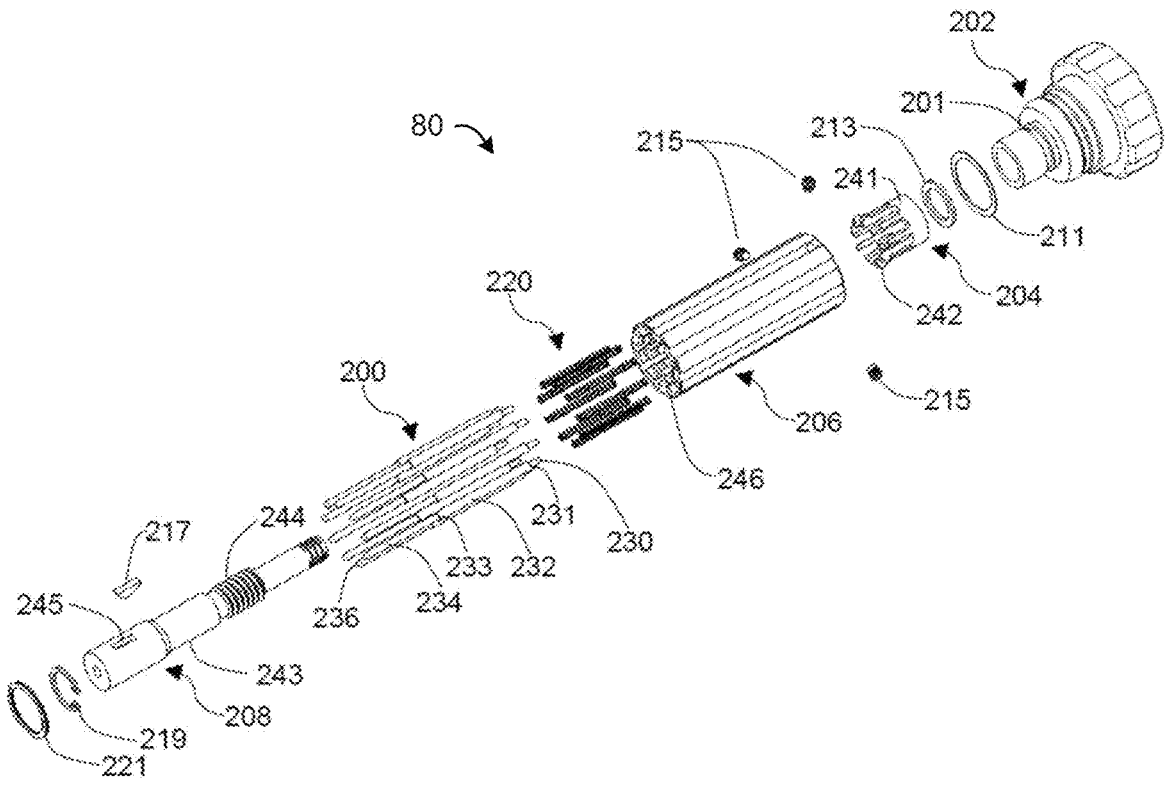
FIG. 11 is a perspective exploded view of the contour guide of FIG. 10.

Turning now to FIGS. 10 and 11, a guide is shown according to one embodiment, which may take the form of a contour guide 80. Contour guide 80 may be designed to capture the topography of a section of a cartilage surface to be replaced. Contour guide 80 may further facilitate alignment of a cutter, such as a trephine, with a section of donor bone and cartilage matching the topography of the resected section, as will be discussed below. In this application, "topography" relates to the three-dimensional shape of at least part of a surface. "Capture" of topography relates to storage of the topography for future use, via any medium, such as mechanical or electrical, storage, including the mechanical storage of a shape in a series of movable surfaces. It will be understood that capturing topography of a section of a cartilage surface does not require capture of the entire surface; rather, capture of the shape of the perimeter of the surface may be sufficient.

The contour guide 80 may have a longitudinal axis that defines a longitudinal axis 83. The contour guide 80 may be helpful for larger graft procedures, in which the surface area of bone and/or cartilage to be replaced is large enough and/or uneven enough to make accurate determination of a normal vector challenging with a guide having fixed legs. Additionally or alternatively, the contour guide 80 may be helpful when the surgeon desires to more accurately match the contour of the cartilage to be replaced, for example, by obtaining a graft from a similar part of a donor bone. Contour guide 80 may facilitate rotational alignment of the graft with the surrounding cartilage of the recipient bone to minimize discontinuities in topology between the graft and the surrounding cartilage.

The contour guide 80 may include a sleeve 206, a lock ring 204, a knob 202, a central pin 208, shim washer 211, thrust washer 213, set screws 215, a woodruff key 217, a retaining ring 219, a sliding pin retaining ring 221, sliding legs 200, and/or springs 220.

Lock ring 204 may have a base 241 located on a proximal end and arms 242 extending distally from base 241. Knob 202 may have a groove 201. Knob 202 may be held within sleeve 206 with set screws 215, which may protrude into groove 201 when knob 202 is rotatably coupled to sleeve 206.

Sleeve 206 may have receptacles 246 configured to receive springs 220 and/or sliding legs 200. Receptacles 246 may be evenly spaced about the periphery of sleeve 206 and may be sufficiently deep to receive and retain sliding legs 200 even when springs 220 are at full (undeflected) length. Central pin 208 may have a pocket 245 configured to receive woodruff key 217, a tapered section 243, and external threads 244.

Each of sliding legs 200 may have a proximal portion 230 adapted to fit into an internal opening of one of springs 220, a central portion 232, a shoulder 231 located between proximal portion 230 and central portion 232 and adapted to abut a distal end of one of springs 220, a distal tip 234, and a shoulder 233 located between central portion 232 and distal tip 234 and adapted to abut sliding pin retaining ring 221 to limit motion of sliding legs 200 distally relative to sleeve 206. Each distal tip 234 may have a distal end 236 adapted to abut cartilage. Each distal tip 234 may, for example, have a rounded and/or hemispherical shape that provides gentle registration on the cartilage surface. The rounded shape may facilitate sliding motion of distal tip 234 against the cartilage surface, for example, to rotate contour guide 80 to a different orientation with the distal tips 236 in engagement with the cartilage surface. As mentioned previously, the hemispherical shape may also provide more predictable point registration. However, in alternative embodiments, a distal tip may have a different shape, including but not limited to cylindrical, conical, parabolic, and ellipsoidal shapes.

Springs 220 may urge the sliding legs 200 to their distal-most position relative to the sleeve 206 such that shoulder 233 contacts the sliding pin retaining ring 221. External threads 244 may mate with internal threads (not shown) in knob 202. Woodruff key 217 may mate with an internal slot (not shown) in sleeve 206 to rotationally lock central pin 208 relative to sleeve 206.

As assembled, tapered section 243 may be in contact with an inwardly-facing surface of each of arms 242. Upon rotating the knob 202 clockwise relative to sleeve 206, central pin 208 may be moved proximally relative to sleeve 206, thus causing tapered section 243 to move proximally relative to lock ring 204, causing arms 242 to flex radially outward and into contact with sliding legs 200. Thus, rotating the knob 202 clockwise may cause sliding legs 200 to transition from an unlocked configuration (i.e., sliding legs 200 may slide longitudinally relative to sleeve 206) to a locked configuration (i.e., sliding legs 200 are prevented from sliding longitudinally relative to sleeve 206). Conversely, rotating the knob 202 counterclockwise may cause the sliding legs 200 to transition from a locked configuration to an unlocked configuration as central pin 208 is moved distally relative to sleeve 206 and arms 242 are permitted to relax into a less deflected or undeflected configuration in which arms 242 do not contact sliding legs 200.

Knob 202, central pin 208, and lock ring 204 may thus cooperate to define a locking mechanism that can be actuated via rotation of knob 202 to move between locked and unlocked configurations. Advantageously, rotation of knob 202 may enable sliding legs 200 to be locked in place without the need to apply direct pressure to the locking mechanism along the longitudinal axis of contour guide 80. Thus, the surgeon can lock sliding legs 200 in place without applying force that could otherwise disturb the positions of sliding legs 200. A "locking mechanism" is any device capable of being actuated to selectively provide mechanical locking.

Figure 12:
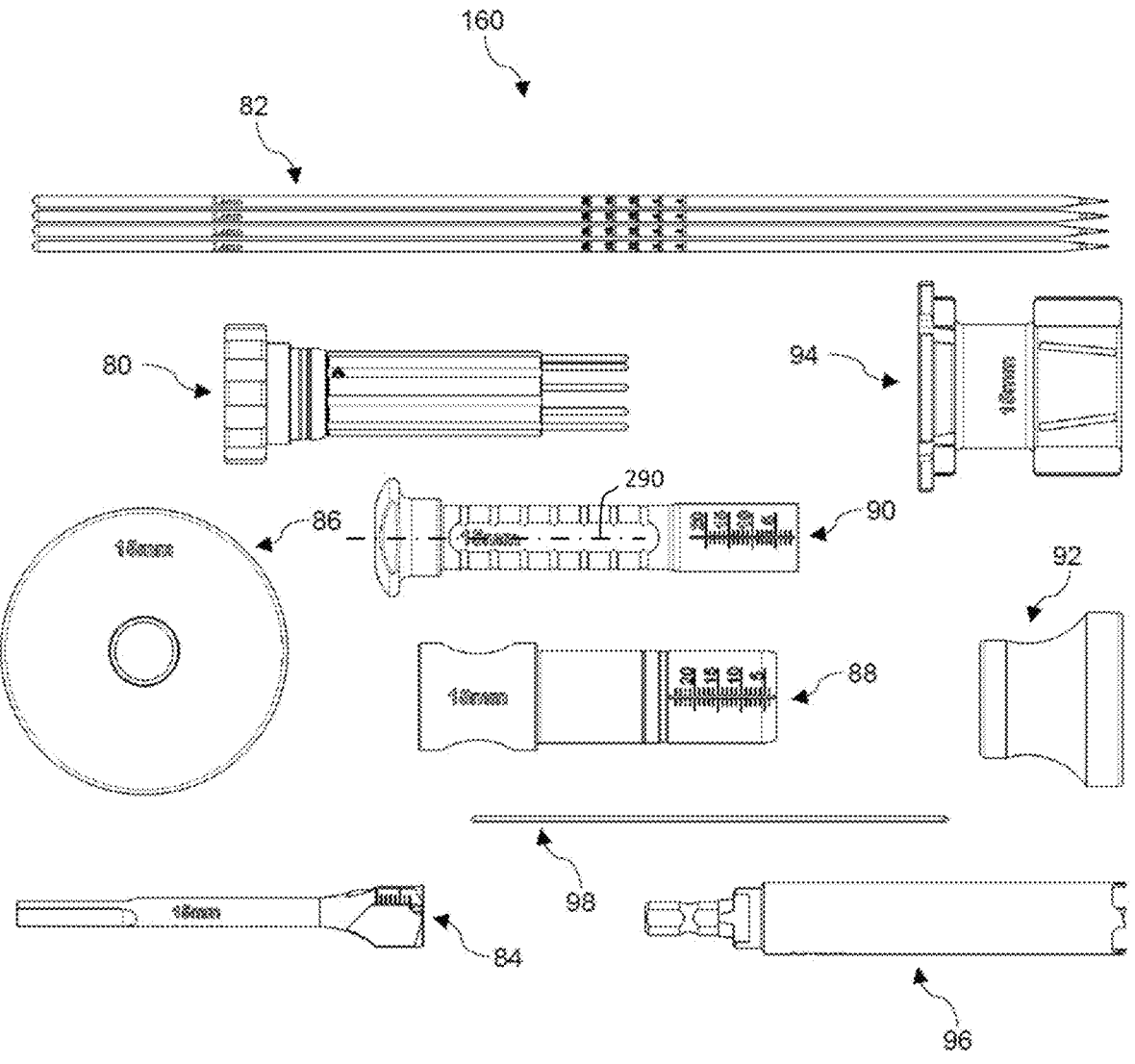
FIG. 12 is a top view of a surgical kit including the contour guide of FIG. 10, according to one embodiment.

FIG. 12 shows a surgical kit 160 and FIGS. 13 through 18B show a method for conducting an osteochondral transfer procedure using the surgical kit 160. The surgical kit 160 in FIG. 12 may include: fixation pins 82, the contour guide 80, a plunger 90, an inserter 88, a cut guide 92, a harvest guide bushing 94, a base 86, a K-wire 98, a cannulated drill 84, and/or a trephine 96. Plunger 90 may have a longitudinal axis 290 and a cannulation 91 extending along longitudinal axis 290. Contour guide 80 may have a cannulation 81 sized to receive a guide pin, such as one of fixation pins 82 and/or K-wire 98, in a close sliding fit.

Figure 13A:
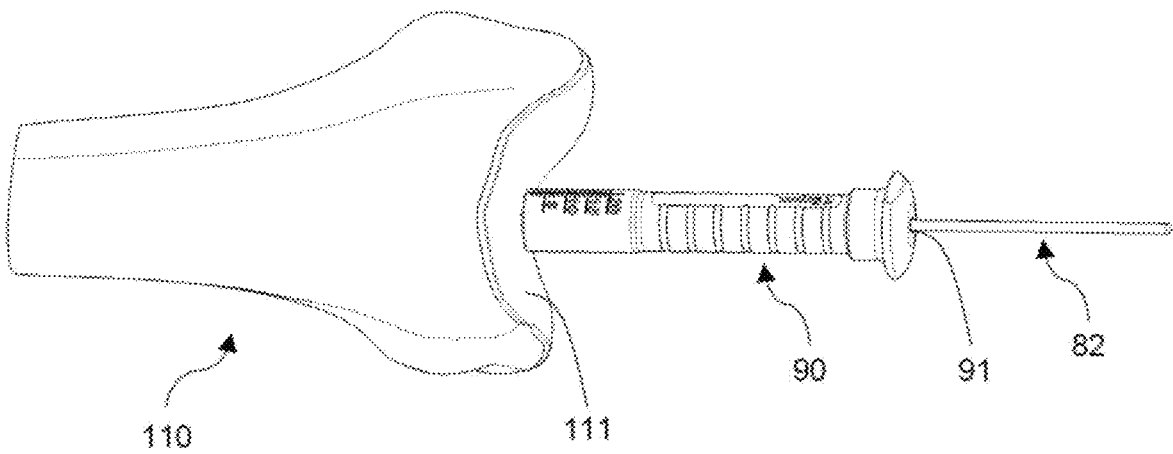
FIG. 13A is a perspective view of the plunger and pin of FIG. 12, and a distal femur.

FIG. 13A shows plunger 90 positioned adjacent to a cartilage surface 111 of a distal femur 110, adjacent to an osteochondral defect. A distal end of plunger 90 may be used to circumscribe the osteochondral defect to confirm the size of the osteochondral defect. Plunger 90 may be used as a pin guide; fixation pin 82 (used as a guide wire) may be placed into cannulation 91 of plunger 90 and then placed centrally into the osteochondral defect and into the underlying bone of distal femur 110. Alternatively, contour guide 80 may be used as a pin guide to place fixation pin 82 in a similar manner. Since the contour of the section of cartilage surface 111 to be replaced will be matched through the use of surgical kit 160, it may not be necessary to ensure perpendicularity of fixation pin 82 relative to cartilage surface 111.

Figure 13B:
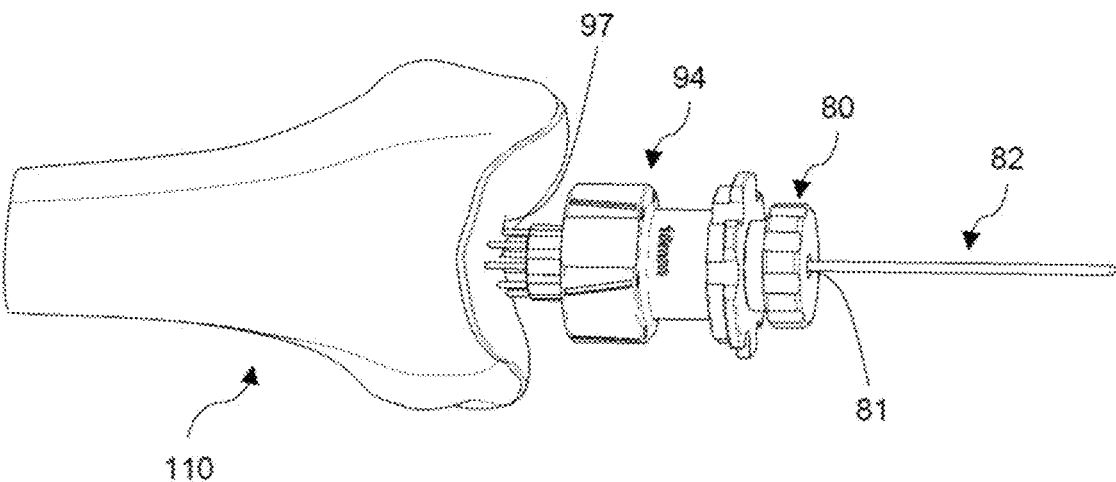
FIG. 13B is a perspective view of the pin, the contour guide, and the harvest guide bushing of FIG. 12, and a distal femur.

With fixation pin 82 in place, contour guide 80 may then be used to identify and/or record the topography of the section of cartilage surface 111 containing and/or covering the osteochondral defect. Specifically, using cannulation 81 of the contour guide 80, the contour guide 80 may be advanced over fixation pin 82 toward the cartilage surface 111 until the distal tips 236 of all sliding legs 200 are in contact with the cartilage surface 111 as shown in FIG. 13B. The springs 220 may urge sliding legs 200 distally, ensuring that the sliding legs 200 remain in contact with cartilage surface 111 as contour guide 80 is advanced toward cartilage surface 111.

Distal tips 236 may contact the cartilage surface 111 within and/or at the edge of the section of cartilage surface 101 that is to be removed. This may advantageously allow distal tips 236 to more accurately follow the contour of the section of cartilage surface 111 that is to be replaced, as compared with devices that register only on the cartilage, outside of the surface to be removed. In some embodiments, the distal tips 236 may contact the edge, itself, of the section of cartilage surface 101 that is to be removed—i.e., not within the section or outside of it, but directly on the boundary defining the section. Such edge contact may provide optimal capture of the topography of the edge of the section, where it will need to meet up with surrounding cartilage. This may help minimize discontinuities occurring at the edge when the section is replaced.

Once all distal tips 236 are in contact with the cartilage surface 111, a clamp (not shown) may be placed on fixation pin 82 just proximal to contour guide 80 to hold contour guide 80 in place. The clamp may be a hemostat, forceps, or other clamps known in the art.

Then, the contour guide 80 may be actuated to transition the sliding legs 200 from an unlocked configuration to a locked configuration as previously described. This may be done, for example, by rotating the knob 202 clockwise so that arms 242 are urged outward, into contact with sliding legs 200 as described previously. Contour guide 80 may have one of the sliding legs 200 designated as an index pin 205, for example, with a marking 207, etching, different color, or other indicator on or adjacent to the index pin (shown in FIG. 10). A recipient index mark 97 can be made on cartilage surface 111 adjacent to the index pin as shown in FIG. 13B, for example, with a surgical pen.

Figure 14A:
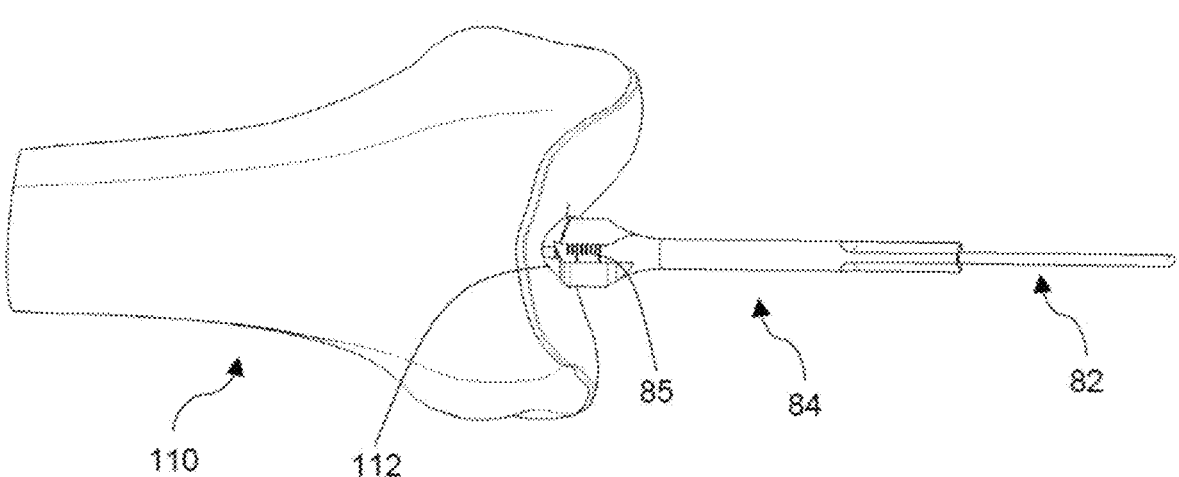
FIG. 14A is a perspective view of the pin and cannulated cutter of FIG. 12, and a distal femur.

Then, the contour guide 80 may be removed from the fixation pin 82. The clamp, if present, may first be removed to allow removal of contour guide 80. Cannulated drill 84 may then be placed over fixation pin 82 and may be used to create a socket 112 having a diameter (DC, not shown) a maximum depth (MD, not shown) in cartilage surface 111 and underlying bone of distal femur 110 at recipient index mark 97 as shown in FIG. 14A. Cannulated drill 84 may have depth marks 85 indicating a distance to a distal end of cannulated drill 84 in order to note MD at recipient index mark 97. MD may be recorded for future use.

Figure 14B:
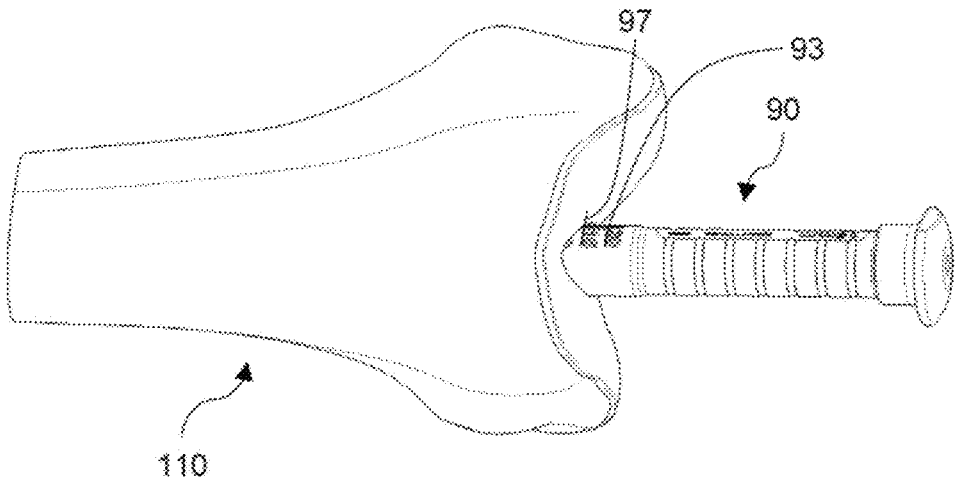
FIG. 14B is a perspective view of the plunger of FIG. 12, and a distal femur.

Plunger 90 may have depth marks 93 indicating the distance to a distal end of plunger 90. Plunger 90 may be inserted into the socket 112 to confirm MD at recipient index mark 97 as shown in FIG. 14B.

Figure 14C:
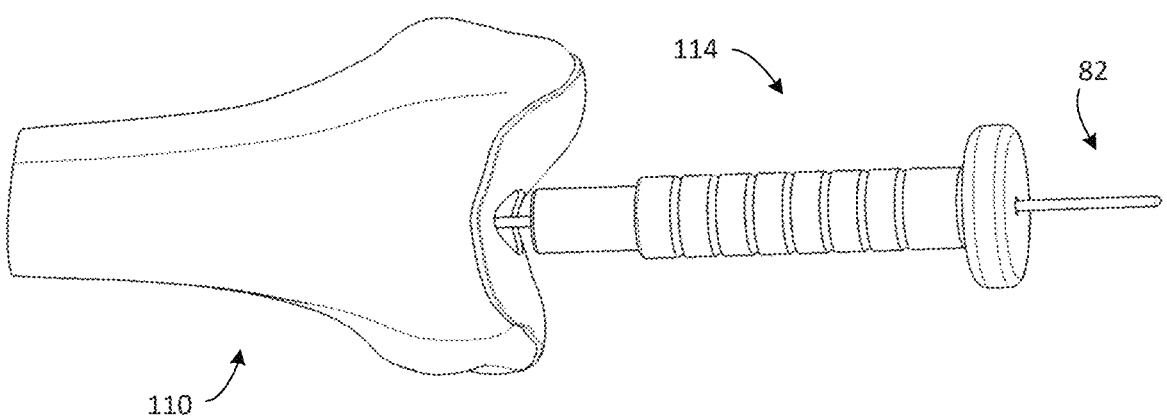
FIG. 14C is a perspective view of the pin of FIG. 12 with a punch.
Figure 14D:
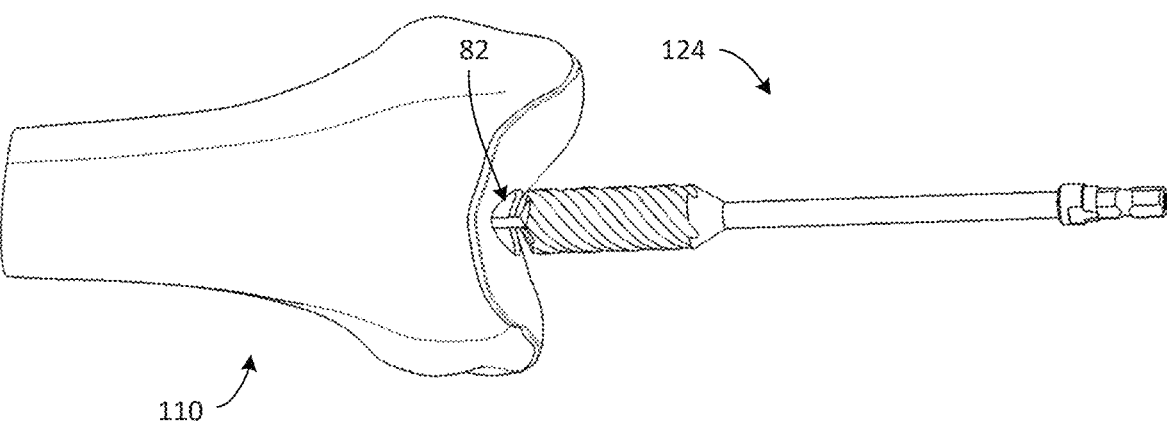
FIG. 14D is a perspective view of the pin of FIG. 12 with an alternative cannulated drill.

In alternative embodiments, other cutter types may be used in place of the cannulated drill 84. For example, as mentioned previously, a trephine may be used, and may be functionally similar to cannulated drill 84, but with a larger cannulation, for example, to preserve some of the removed bone and/or cartilage. As shown in FIGS. 14C and 14D, a punch 114 or an alternative cannulated drill 124 may be used. Like cannulated drill 84, punch 114 and alternative cannulated drill 124 may slide over guide pin 82 to remove the desired bone and/or cartilage from distal femur 110. Alternative cannulated drill 124 may be rotated during insertion to cut with rotary action, like cannulated drill 84. Punch 114 may be impacted or otherwise driven into distal femur 110 to create an annular bore around the bone and/or cartilage to be removed. If desired, with any of the cutters set forth above, other instruments may then be used to remove the bone/cartilage plug from distal femur 110.

Figure 15A:
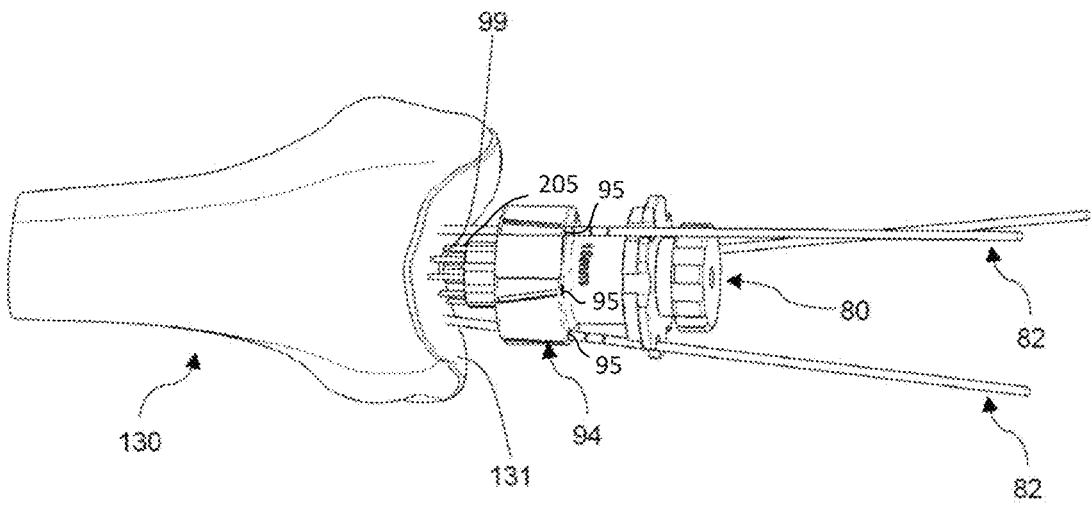
FIG. 15A is a perspective view of the contour guide, harvest guide bushing, and fixation pins of FIG. 12, and a distal femur.

Next, the harvest guide bushing 94 may be connected to the contour guide 80 as shown in FIG. 15A, and then the contour guide 80 may be positioned on a cartilage surface 131 of a distal femur allograft 130 such that all distal tips 236, or substantially all, of distal tips 236, are in contact with cartilage surface 131 as shown in FIG. 15A (referred to herein as "fully registered"). Advantageously, the distal femur allograft 130 selected may be the same anatomic structure of similar size and cartilage surface morphology as distal femur 110. For example, if the recipient site is a trochlear groove of a distal femur, the allograft selected may be a portion of a similar size distal femur that includes a trochlear groove portion having a similar cartilage surface morphology.

Because distal femur allograft 130 and distal femur 110 may not have precisely the same shape, it is possible that not all distal tips 236 can be simultaneously placed in contact with cartilage surface 131. In such a case, the surgeon will position contour guide 80 such that distal tips 236 are all placed as close as possible to cartilage surface 131, so that distal tips 236 are positioned about the periphery of an area very similar in shape to the defective bone and cartilage removed from distal femur 110. In such a configuration, sliding legs 200 will also be considered "fully registered."

Once the contour guide 80 is fully registered with cartilage surface 131 of distal femur allograft 130 as shown in FIG. 15A, the harvest guide bushing 94 may be secured to distal femur allograft 130 by placing fixation pins 82 through pin receptacles 95 in the harvest guide bushing 94 and into the distal femur allograft 130. Additionally, or alternatively, a holding mechanism (not shown) may be used to secure distal femur allograft 130 and also secure the harvest guide bushing 94 in a desired relative position. In this application, a "guide bushing" refers to a structure capable of being fixed to a bone in a predetermined location to guide motion of another object, such as trephine 96.

Figure 15B:
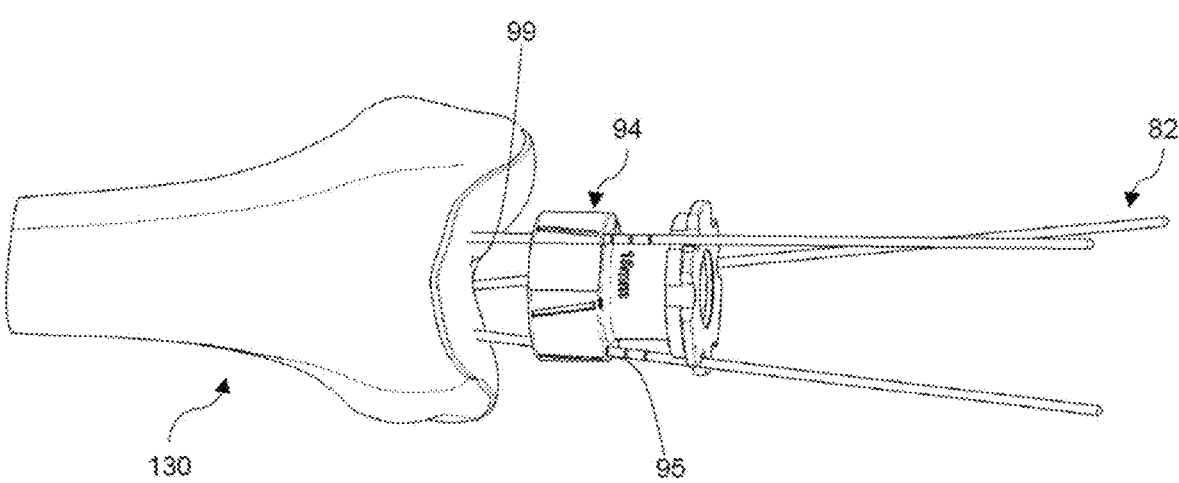
FIG. 15B is a perspective view of the items of FIG. 15A, with the contour guide removed.
Figure 16A:
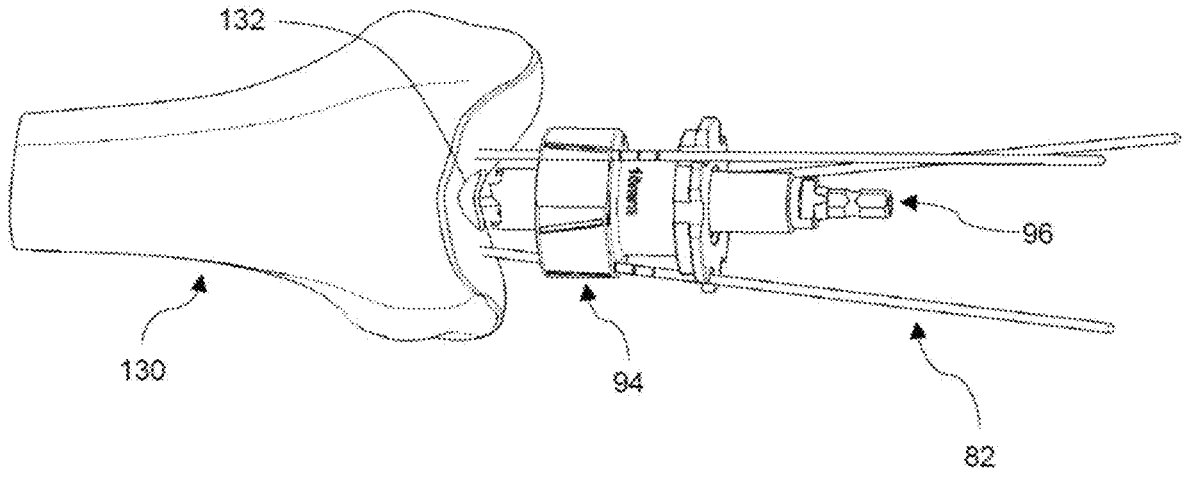
FIG. 16A is a perspective view of the harvest guide bushing, fixation pins, and trephine of FIG. 12, and a distal femur.
Figure 16B:
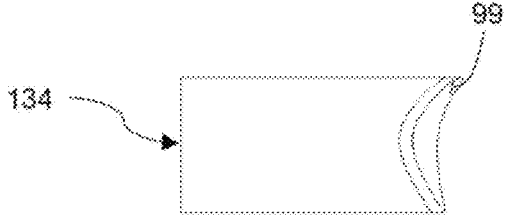
FIG. 16B is a side elevation view of an osteochondral graft according to one embodiment.

Next, a donor index mark 99 may be made next to the index pin 205 as shown in FIGS. 15A and 15B. Then, the contour guide 80 may be removed proximally from the harvest guide bushing 94 as shown in FIG. 15B. An outer surface of trephine 96 may be guided by an inner surface of harvest guide bushing 94 to cut an outer cylinder wall having a diameter DC of an osteochondral graft 134 as shown in FIG. 16A. Trephine 96 may be inserted into distal femur allograft 130 until trephine extends at least MD into distal femur allograft 130. Then, a saw blade (not shown) may be used to cut a distal end of the osteochondral graft 134 that is transverse to the outer cylinder wall to form an osteochondral graft 134 that has been harvested as shown in FIG. 16B.

Next, inserter 88 may be connected to base 86, and osteochondral graft 134 may be inserted into the distal end of the inserter 88 with a cartilage end of the osteochondral graft 134 positioned proximally as shown in FIGS. 17A, 17B, and 17C (the distal end of the inserter 88 is facing up and the proximal end of the inserter 88 is facing down in FIGS. 17A, 17B, and 17C). The osteochondral graft 134 may be positioned within the inserter 88 so that the most proximal portion of the cartilage at donor index mark 99 aligns with a depth mark 89 on the inserter 88 that is equal to MD as shown in FIG. 17B. Then, the cut guide 92 may be installed onto the distal end of the inserter 88 until a resilient member on cut guide 92 engages an external groove on the inserter 88 as described in connection with FIGS. 8A, 8B, and 8C. Alternatively, the cut guide 92 may be integral to the inserter 88, or other alternative configurations may be employed as set forth previously.

Advantageously, the distance between the distal (top) surface of the cut guide 92 and the depth mark corresponding to the proximal end of the osteochondral graft 134 is equal to MD. Then, a saw blade (not shown) may be used to trim the length of the osteochondral graft 134 flush with the distal (top) surface of the cut guide 92, thus creating an osteochondral graft 134 having a maximum length equal to MD. Optionally, a K-wire 98 may be placed through a hole (not shown) in the side of cut guide 92 and into the side of osteochondral graft 134 to secure the osteochondral graft 134 during the cutting operation.

Next, the cut guide 92 may be removed from the distal end of the inserter 88, and the plunger 90 may be inserted into the proximal end of the inserter 88. The distal end of the osteochondral graft 134 and inserter 88 may then be placed adjacent to the socket 112 so that donor index mark 99 and/or depth mark 89 align with recipient index mark 97, and the plunger 90 may be used to expel the osteochondral graft 134 from the inserter 88 and into the socket 112 until a cartilage surface of the osteochondral graft 134 is flush with the portion of cartilage surface 111 surrounding the socket 112 as shown in FIGS. 18A and 18B. Alternatively, the plunger 90 may be used to expel the osteochondral graft 134 from the inserter 88, and the osteochondral graft 134 may be placed into socket 112 by hand while aligning donor index mark 99 with recipient index mark 97. Alternatively, in the absence of donor index mark 99 and recipient index mark 97, osteochondral graft 134 can be partially inserted by hand into socket 112, rotated until the contour of the graft matches the portion of cartilage surface 111 surrounding the socket 112 with a consistent offset, and then be pressed into final position, flush with the cartilage surrounding the socket 112.

While the foregoing discussion is focused on circular osteochondral lesions and cylindrical osteochondral grafts, the systems, devices and methods discussed herein may also be adapted to work with non-circular osteochondral lesions and non-cylindrical osteochondral grafts. For osteochondral lesions that may be circumscribed by a perimeter shape that is non-circular, a socket may be formed at a recipient site with a cutting tool having a matching perimeter shape, and an osteochondral graft may be formed at a donor site having a matching perimeter shape and transferred to the socket at the recipient site. For non-circular perimeter shapes, cutting tools for forming a socket or an osteochondral graft may be in the form of a punch (not shown), which cuts by translating along a working axis, as opposed to a rotary cutter used for a cylindrical form that cuts by rotating about a working axis.

Figure 19A:
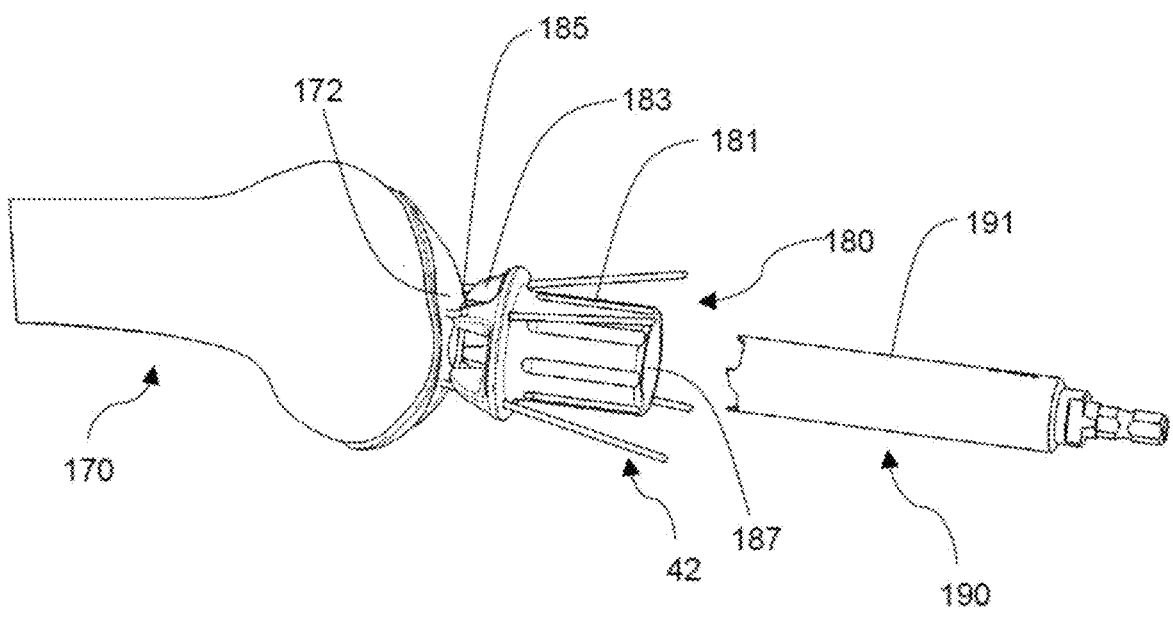
FIG. 19A is a perspective view of a guide bushing and a trephine according to one embodiment, and a distal femur.
Figure 19B:
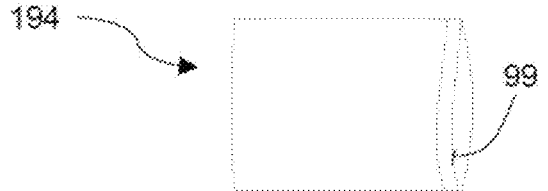
FIG. 19B is a side elevation view of an osteochondral graft according to one embodiment.

As an alternative to the osteochondral graft 104 with a cylindrical shape as discussed above, a custom osteochondral graft 194 may be formed, which may advantageously provide a cartilage topography that may be a better topographical match for a graft recipient site. As shown in FIG. 19A, guide bushing 180 may have a body 181, an internal surface 187 extending through body 181 along a long axis of body 181, four legs 183 extending distally from body 181, and distal tips 185 located on the distal end of legs 183. FIG. 19A shows the guide bushing 180 with all four distal tips 185 in contact with a cartilage surface 172 of a distal femur 170, and guide bushing 180 held in place by guide pins 42. A trephine 190, also known as a graft harvesting tool, may have an external surface 191 that is guided by internal surface 187 to cut an outer cylinder wall having a diameter DP of a custom osteochondral graft 194 as shown in FIG. 19A. Then, a saw blade (not shown) may be used to cut a distal end of the custom osteochondral graft 194 that is transverse to the outer cylinder wall at a length PD to form a custom osteochondral graft 194 as shown in FIG. 19B. A donor index mark 99 may be placed on a cartilage surface of custom osteochondral graft 194 as previously discussed.

The foregoing discussion used osteochondral repairs to the distal femur as an illustrative example. The systems, devices and methods discussed herein may also be used for osteochondral repairs for any diarthrodial joint location, such as those found in the foot, ankle, knee, hip, shoulder, elbow, wrist, and hand.

FIG. 20 shows a flowchart 203 depicting an osteochondral repair method suitable for the surgical kit 140 of FIG. 5. Notably, the method of flowchart 203 may be used with alternative systems, and the surgical kit 140 of FIG. 5 may be used with alternative methods.

In step 210, a pin guide having a central cannulation and four discrete distal tips may be positioned such that all four distal tips are in contact with a recipient cartilage surface having an osteochondral defect, and such that all four distal tip are positioned about a periphery of the cartilage defect. In step 222, a guide pin may be placed through the guide feature (for example, a central cannulation) of the pin guide and through the cartilage defect into an underlying bone substrate. In step 235, using a cannulated cutter guided by the guide pin, a socket may be created through the recipient cartilage surface by removing the cartilage defect, wherein the socket has an inner peripheral shape and a predetermined depth. In step 240, using a donor graft that has an outer peripheral shape that corresponds to the inner peripheral shape and a length that is substantially transverse to the outer peripheral shape and substantially equal to the predetermined depth, the donor graft may be inserted into the socket.

FIG. 21 shows a flowchart 300 depicting an osteochondral repair method suitable for the surgical kit 160 of FIG. 12. Notably, the method of flowchart 300 may be used with alternative systems, and the surgical kit 160 of FIG. 12 may be used with alternative methods.

In step 310, a contour guide having an index feature and mobile contact surfaces may be positioned against a section of a recipient cartilage surface having a recipient topography to transfer the recipient topography to the contact surfaces. In step 320, a recipient index mark may be created on the recipient cartilage surface adjacent to the index feature and the contact surfaces may be immobilized. In step 330, the contour guide may be positioned against a donor cartilage surface (for example, of a bulk graft), so that immobilized contact surfaces are all substantially in contact with the donor cartilage surface. In step 340, a donor index mark may be created on the donor cartilage surface adjacent to the index feature. In step 350, a donor graft may be formed from the bulk graft that has an outer peripheral shape that corresponds to the inner peripheral shape. In step 360, a socket having an inner peripheral shape may be created through the recipient cartilage surface to remove the cartilage defect. In step 370, a socket depth of the socket may be measured from the recipient cartilage surface to a bottom of the socket at the recipient index mark. In step 380, a length of the donor graft may be formed so that the length is substantially transverse to the outer peripheral shape and substantially equal to the socket depth at the recipient index mark. In step 390, the donor graft may be inserted into the socket while aligning the donor index mark to the recipient index mark. Alternatively, in the absence of a donor index mark and a recipient index mark, the prepared donor graft can be partially inserted by hand into the socket, and then rotated until the contour of the donor graft matches the surface of cartilage surrounding the socket with a consistent offset and then be pressed into final position.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment. Features and/or method steps of the various embodiments set forth above may be combined together to yield new embodiments. The drawings are drawn to scale, but the shapes and dimensions shown in the drawings are merely exemplary. Various features and/or dimensions may be modified within the understanding of a person of ordinary skill in the art with the aid of the present disclosure.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. Moreover, as defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A system for osteochondral defect repair, the system comprising:
   a guide comprising:
      a first leg;
      a second leg;
      a third leg;
      a fourth leg; and
      a guide feature;
   wherein:
      the first leg, the second leg, the third leg, and the fourth leg each comprise a distal tip at a fixed location relative to the guide feature;
      the distal tips of the first leg, the second leg, the third leg, and the fourth leg lie in a plane;
      the distal tips are configured to contact a cartilage surface on a first bone independently of contact between the cartilage surface and any other distal tip besides the distal tips of the first leg, the second leg, the third leg, and the fourth leg; and
      the guide feature is oriented to define a working axis, perpendicular to the plane, along which a cutter is movable to remove bone and cartilage from a first bone.

2. The system of claim 1, wherein the guide feature comprises a cannulation passing through the guide;
   wherein:
      the cannulation is parallel to the working axis;
      the cannulation is configured to guide a pin along the working axis; and
      the cannulation is sized to receive the pin with a close sliding fit.

3. The system of claim 2, further comprising the cutter;
   wherein:
      the cutter is one of a trephine, a drill, and a punch; and
      the cutter is configured to be guided by the pin along the working axis.

4. The system of claim 3, wherein:
   the first bone is a recipient bone; and
   the cutter is configured to remove a section of the recipient bone containing an osteochondral defect and to leave a socket suitable for receiving an osteochondral graft.

5. The system of claim 1, further comprising a cutting guide;
   wherein:
      the cutting guide is configured to receive an osteochondral graft; and
      the cutting guide is configured to guide further cutting of the osteochondral graft.

6. The system of claim 5, wherein the cutting guide comprises:
   an aperture configured to receive the osteochondral graft; and
   a distal surface configured to guide a saw blade to cut the osteochondral graft to a desired length that matches a depth of a socket formed in a recipient bone from removal of a section of the recipient bone containing an osteochondral defect.

7. The system of claim 6, further comprising an inserter configured to receive the osteochondral graft and deliver the osteochondral graft to the socket;

wherein the inserter is configured to mate with the cutting guide such that the inserter receives the osteochondral graft as the osteochondral graft is inserted into the aperture.

8. The system of claim 1, further comprising an inserter and a plunger;

wherein:

the inserter is configured to receive an osteochondral graft; and the plunger is configured to push the osteochondral graft out of the inserter and deposit the osteochondral graft into a socket formed in a recipient bone from removal of a section of the recipient bone containing an osteochondral defect.

9. The system of claim 1, further comprising the cutter;

wherein:

the cutter is a one of a trephine, a drill, and a punch;

the guide feature comprises a cannulation passing through the guide; and the cannulation is sized to receive the cutter with a close sliding fit.

10. A system for osteochondral defect repair, the system comprising:

a cutter configured to slide along a pin to remove bone and cartilage from a first bone; and a guide configured to guide placement of the pin, the guide comprising:

a first leg;

a second leg;

a third leg;

a fourth leg; and a guide feature;

wherein:

the first leg, the second leg, the third leg, and the fourth leg each comprise a distal tip at a fixed location relative to the guide feature;

the distal tips of the first leg, the second leg, the third leg, and the fourth leg lie in a plane; and the guide feature is oriented to guide placement of the pin along a working axis perpendicular to the plane.

11. The system of claim 10, wherein the guide feature comprises a cannulation passing through the guide;

wherein:

the cannulation is parallel to the working axis;

the cannulation is configured to guide the pin along the working axis; and the cannulation is sized to receive the pin with a close sliding fit.

12. The system of claim 11, further comprising the pin;

wherein:

the cutter is a one of a trephine, a drill, and a punch, and the pin is configured to guide motion of the cutter along the working axis.

13. The system of claim 12, wherein:

the first bone is a recipient bone; and the cutter is configured to remove a section of the recipient bone containing an osteochondral defect and to leave a socket suitable for receiving an osteochondral graft.

14. The system of claim 10, further comprising a cutting guide;

wherein:

the cutting guide is configured to receive an osteochondral graft; and the cutting guide is configured to guide further cutting of the osteochondral graft.

15. The system of claim 14, wherein the cutting guide comprises:

an aperture configured to receive the osteochondral graft; and a distal surface configured to guide a saw blade to cut the osteochondral graft to a desired length that matches a depth of a socket formed in a recipient bone from removal of a section of the recipient bone containing an osteochondral defect.

16. The system of claim 15, further comprising an inserter configured to receive the osteochondral graft and deliver the osteochondral graft to the socket;

wherein the inserter is configured to mate with the cutting guide such that the inserter receives the osteochondral graft as the osteochondral graft is inserted into the aperture.

17. The system of claim 10, further comprising an inserter and a plunger;

wherein:

the inserter is configured to receive an osteochondral graft; and the plunger is configured to push the osteochondral graft out of the inserter and deposit the osteochondral graft into a socket formed in a recipient bone from removal of a section of the recipient bone containing an osteochondral defect.

18. A method of repairing an osteochondral defect, the method comprising:

positioning a guide having four distal tips over a cartilage surface so that the four distal tips are positioned about a periphery of a section of the cartilage surface on a first bone;

placing the guide so that three of the distal tips are in contact with the cartilage surface;

rotating the guide until all four of the distal tips are in contact with the cartilage surface; and using the guide to guide a cutter to remove the section from the first bone.

19. The method of claim 18, wherein:

the four distal tips are positioned on an end of each of four legs;

the four distal tips define a plane; and rotating the guide comprises positioning the plane parallel to the section of the cartilage surface.

20. The method of claim 18, wherein using the guide to guide the cutter comprises guiding the cutter along a working axis perpendicular to the section of the cartilage surface.

21. The method of claim 20, wherein using the guide to guide the cutter comprises:

using the guide to guide insertion of a pin along the working axis into the first bone; and using the pin to guide the cutter along the working axis to remove the section.

22. The method of claim 18, wherein:

the first bone is a recipient bone; and removing the section comprises removing the osteochondral defect to leave a socket suitable for receiving an osteochondral graft.

23. The method of claim 22, further comprising:

Inserting the osteochondral graft into a cutting guide; and using the cutting guide to cut the osteochondral graft to fit the socket.

24. The method of claim 23, wherein:

the cutting guide comprises an aperture and a distal surface;

inserting the osteochondral graft into the cutting guide comprises inserting the osteochondral graft into the aperture; and cutting the osteochondral graft comprises guiding a saw blade along the distal surface to cut the osteochondral graft to a desired length that matches a depth of the socket.

25. The method of claim 24, further comprising mating the cutting guide with an inserter such that the inserter receives the osteochondral graft as the osteochondral graft is inserted into the aperture; and using the inserter to insert the osteochondral graft into the socket.

26. The method of claim 18, further comprising:

inserting an osteochondral graft into an inserter; and using a plunger to urge the osteochondral graft out of the inserter and into a socket formed in a recipient bone from removal of the section of the recipient bone containing the osteochondral defect.

27. A method of repairing an osteochondral defect, the method comprising:

positioning a guide having four distal tips over a cartilage surface so that the four distal tips are positioned about a periphery of a section of the cartilage surface on a first bone;

placing the guide so that the distal tips are in contact with the cartilage surface, with two distal tips on each side of a plane of symmetry of the cartilage surface; and using the guide to guide a cutter to remove the section from the first bone.

28. The method of claim 27, wherein:

each of the four distal tips is positioned on an end of one of four legs;

the four distal tips define a plane; and using the guide to guide the cutter comprises guiding the cutter along a working axis perpendicular to the section of the cartilage surface.

29. The method of claim 27, wherein using the guide to guide the cutter comprises:

using the guide to guide insertion of a pin along a working axis into the first bone; and using the pin to guide the cutter along the working axis to remove the section.

30. A system for osteochondral defect repair, the system comprising:

a guide comprising:

a first leg;

a second leg;

a third leg;

a fourth leg; and a guide feature;

wherein:

the first leg, the second leg, the third leg, and the fourth leg each comprise a distal tip at a fixed location relative to the guide feature such that the distal tips are movable into contact with cartilage on a perimeter of a section of a first bone;

the distal tips of the first leg, the second leg, the third leg, and the fourth leg lie in a plane; and the guide feature is oriented to define a working axis, perpendicular to the plane, along which a cutter is movable to remove the section of bone and cartilage from the first bone.

31. The system of claim 30, wherein the guide feature comprises a cannulation passing through the guide;

wherein:

the cannulation is parallel to the working axis;

the cannulation is configured to guide a pin along the working axis; and the cannulation is sized to receive the pin with a close sliding fit.

32. The system of claim 31, further comprising the cutter;

wherein:

the cutter is one of a trephine, a drill, and a punch; and the cutter is configured to be guided by the pin along the working axis.

33. The system of claim 30, further comprising a cutting guide;

wherein:

the cutting guide is configured to receive an osteochondral graft; and the cutting guide is configured to guide further cutting of the osteochondral graft.

34. The system of claim 30, further comprising an inserter and a plunger;

wherein:

the inserter is configured to receive an osteochondral graft; and the plunger is configured to push the osteochondral graft out of the inserter and deposit the osteochondral graft into a socket formed in a recipient bone from removal of a section of the recipient bone containing an osteochondral defect.

* * * * *